United States Patent [19]
Ishikawa et al.

[11] Patent Number: 6,123,657
[45] Date of Patent: Sep. 26, 2000

[54] MAGNETIC STIMULATING APPARATUS FOR A LIVING BODY

[75] Inventors: Norio Ishikawa; Hidehiro Hosaka; Hiroichi Nakamura; Keiichiro Kon, all of Tokyo, Japan

[73] Assignee: Nihon Kohden Corporation, Tokyo, Japan

[21] Appl. No.: 08/958,248

[22] Filed: Oct. 27, 1997

[30] Foreign Application Priority Data

Oct. 25, 1996 [JP] Japan .................................. 8-283890

[51] Int. Cl.[7] .............................. A61B 17/52; A61N 2/00
[52] U.S. Cl. ................................................................ 600/9
[58] Field of Search .................................. 600/9–15

[56] References Cited

U.S. PATENT DOCUMENTS

| | | |
|---|---|---|
| 4,537,181 | 8/1985 | Shalhoob et al. ........................ 600/9 |
| 4,727,857 | 3/1988 | Horl .......................................... 600/9 |
| 5,632,720 | 5/1997 | Kleitz ..................................... 600/9 X |
| 5,667,469 | 9/1997 | Zhang et al. ............................ 600/9 |

FOREIGN PATENT DOCUMENTS 3-67423   10/1991   Japan .

*Primary Examiner*—Samuel Gilbert
*Attorney, Agent, or Firm*—Sughrue, Mion, Zinn, MacPeak & Seas, PLLC

[57] ABSTRACT

When a motor 2 rotates, a permanent magnet 4a held by a magnet holding member 3a is rotated. When a case 1 is caused to approach the living body 6 under this state, a varying magnetic field is generated in the living body 6 and eddy currents are generated, thereby treating the patient.

36 Claims, 26 Drawing Sheets

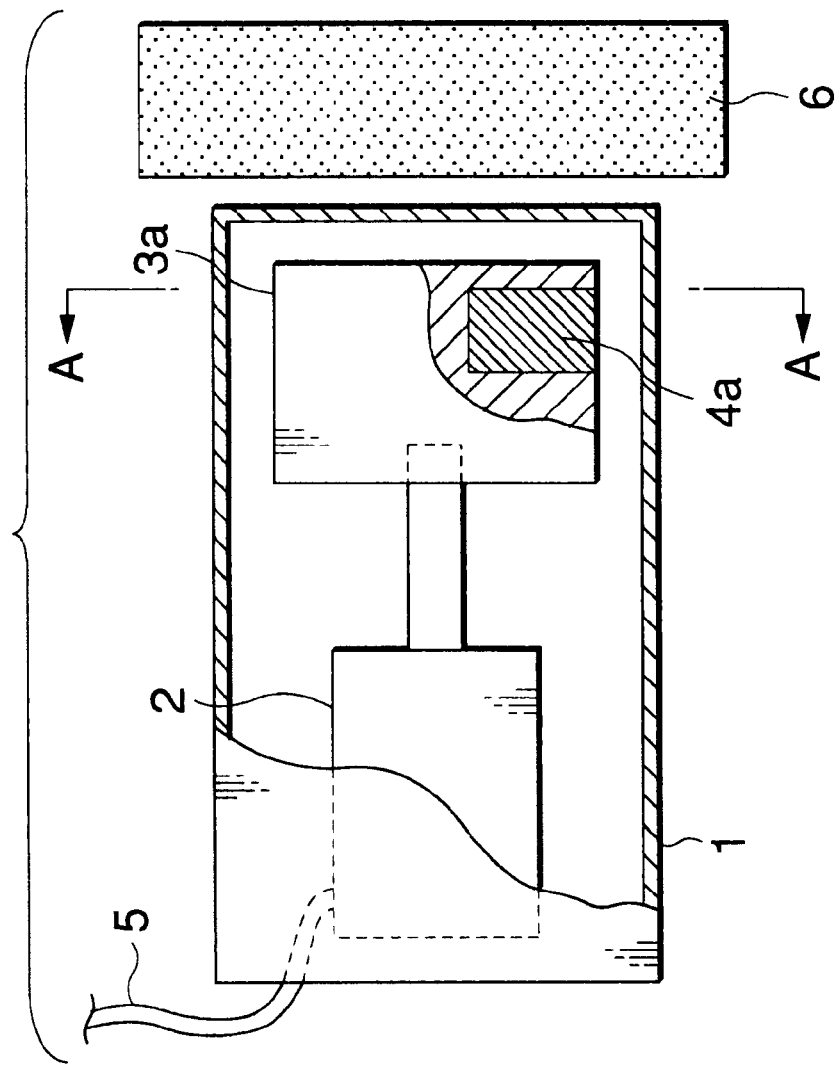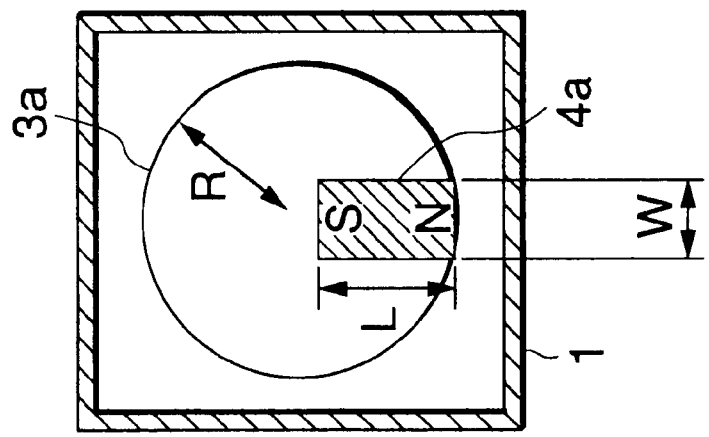

FIG.2
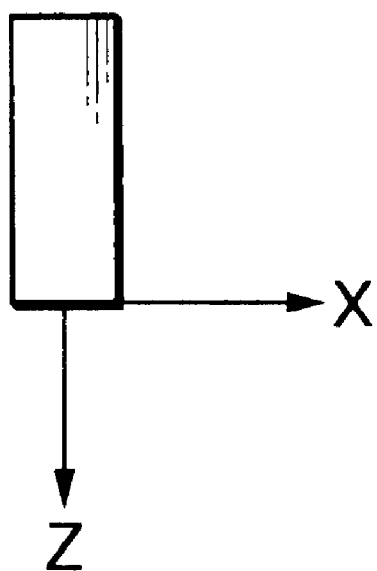
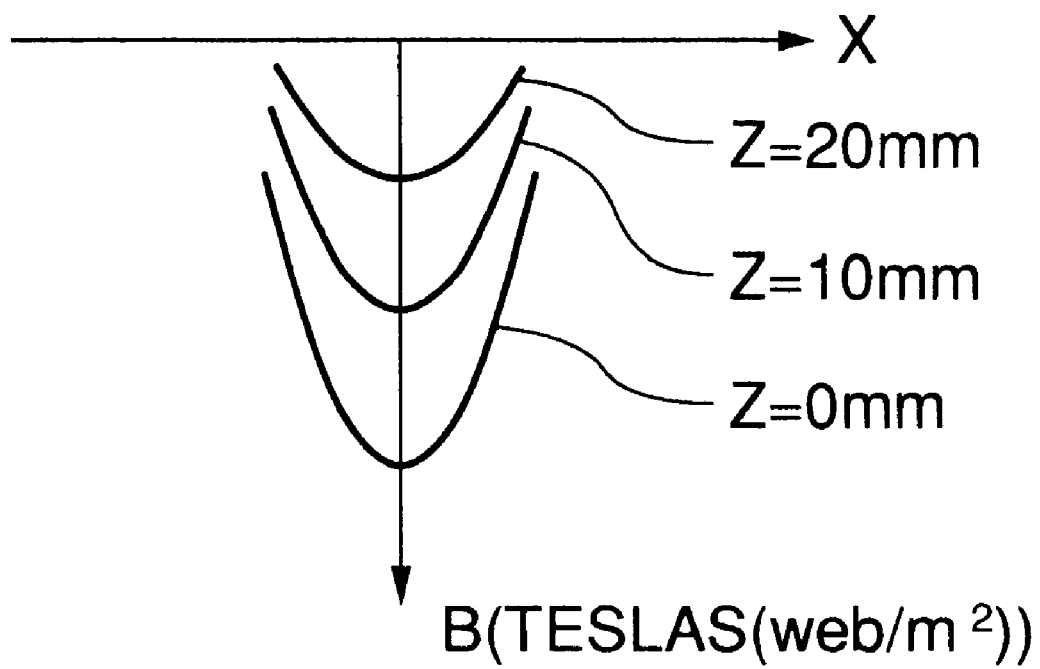

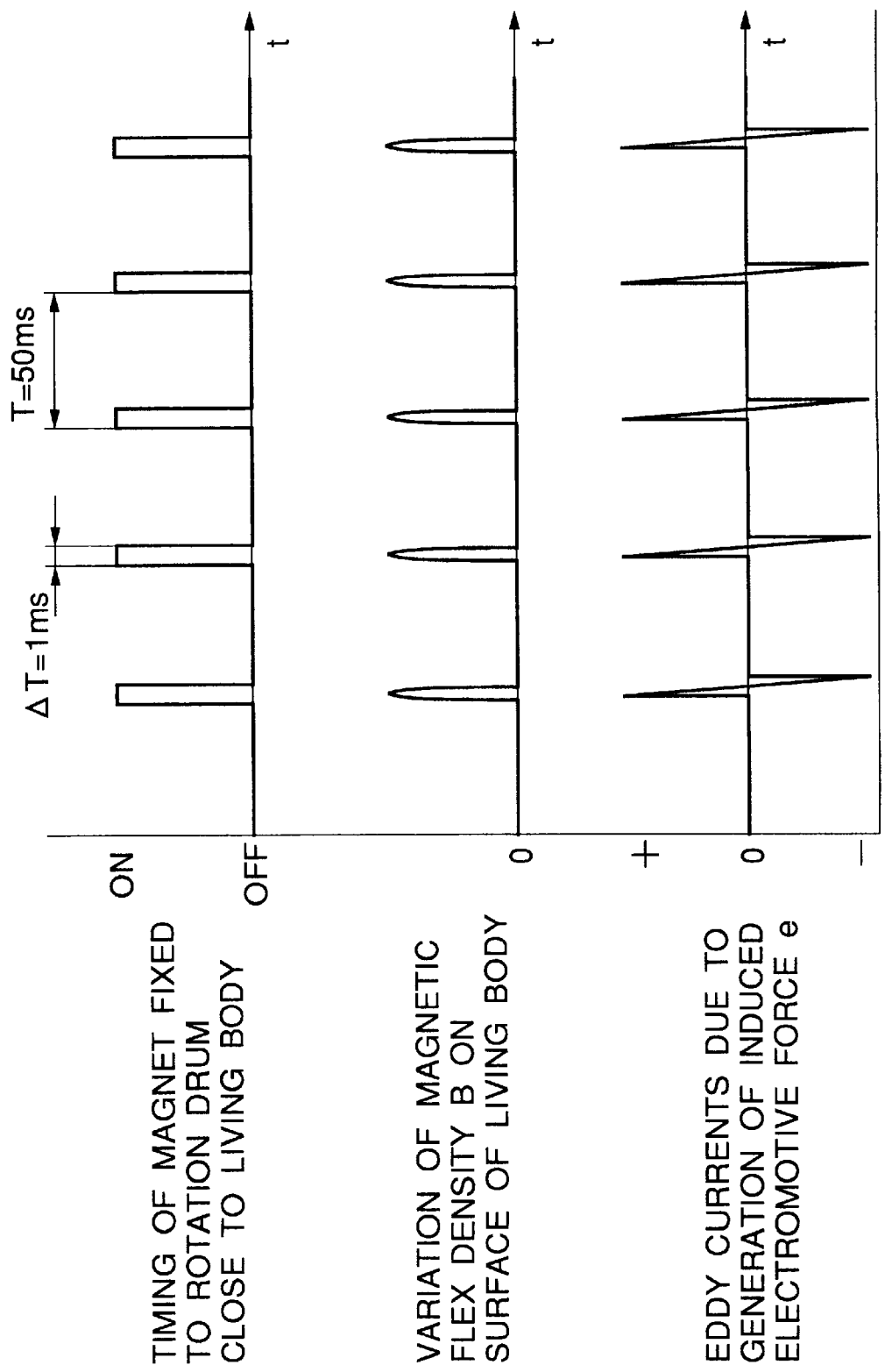

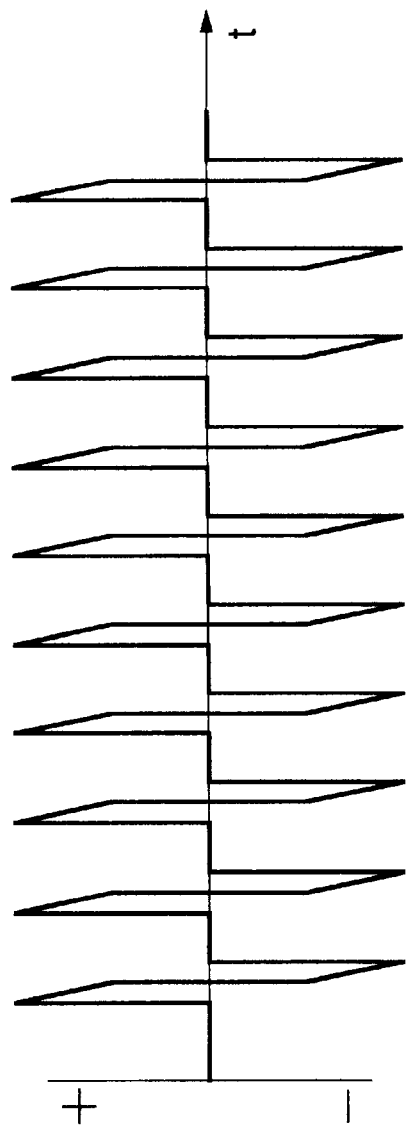

FIG.15(a)

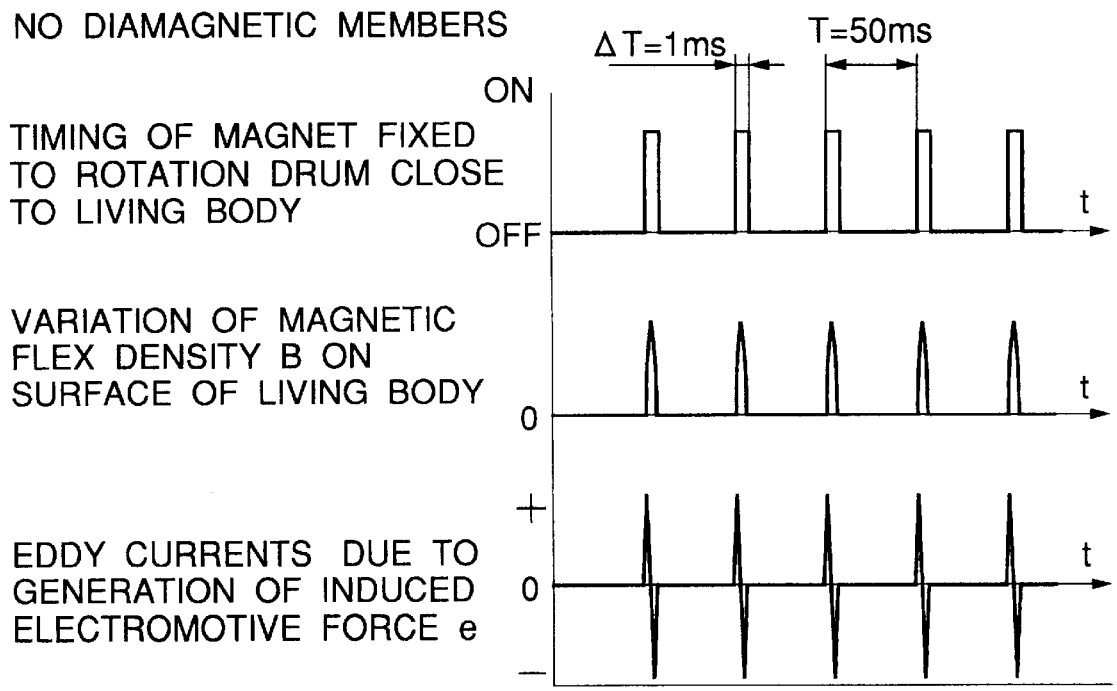

NO DIAMAGNETIC MEMBERS

TIMING OF MAGNET FIXED TO ROTATION DRUM CLOSE TO LIVING BODY

VARIATION OF MAGNETIC FLEX DENSITY B ON SURFACE OF LIVING BODY

EDDY CURRENTS DUE TO GENERATION OF INDUCED ELECTROMOTIVE FORCE e

FIG.15(b)

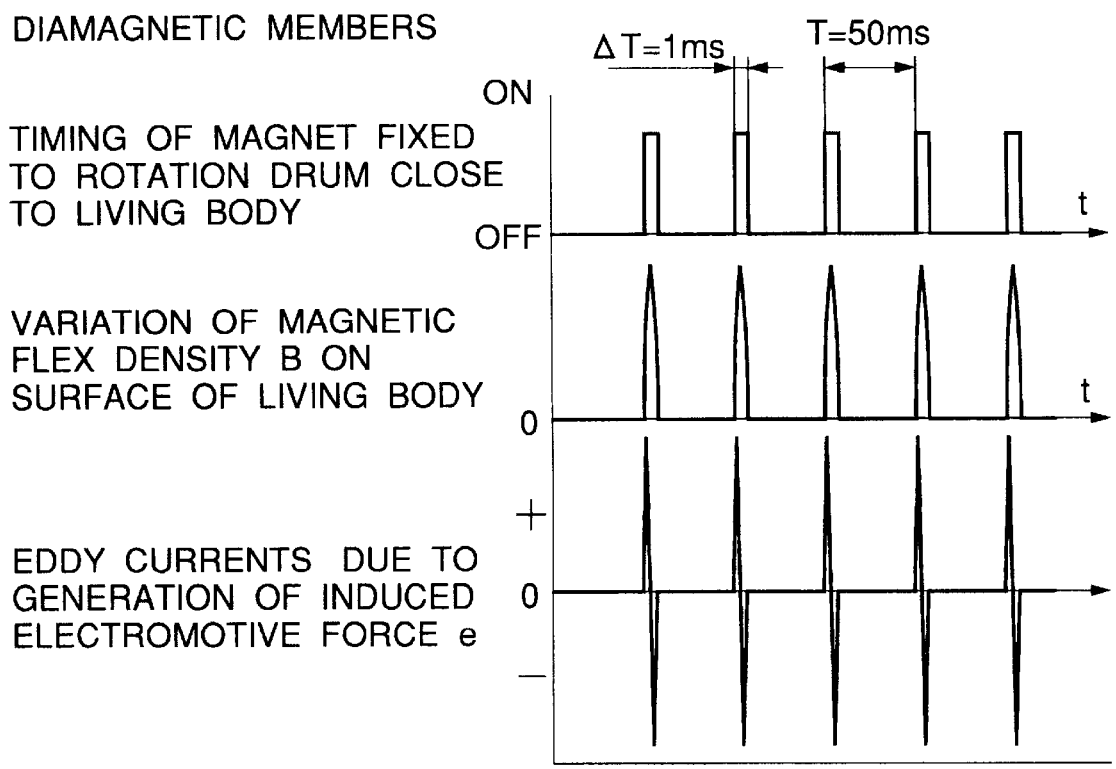

DIAMAGNETIC MEMBERS

TIMING OF MAGNET FIXED TO ROTATION DRUM CLOSE TO LIVING BODY

VARIATION OF MAGNETIC FLEX DENSITY B ON SURFACE OF LIVING BODY

EDDY CURRENTS DUE TO GENERATION OF INDUCED ELECTROMOTIVE FORCE e

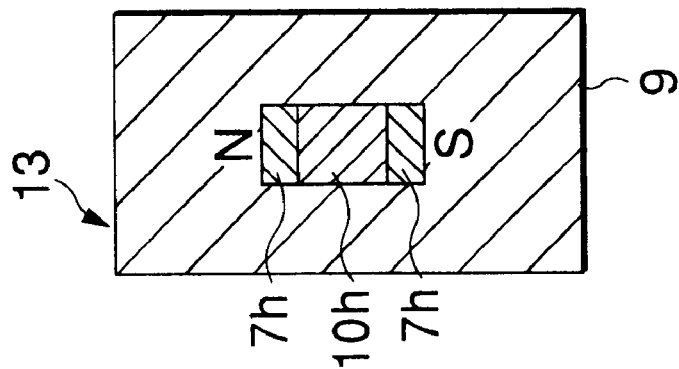
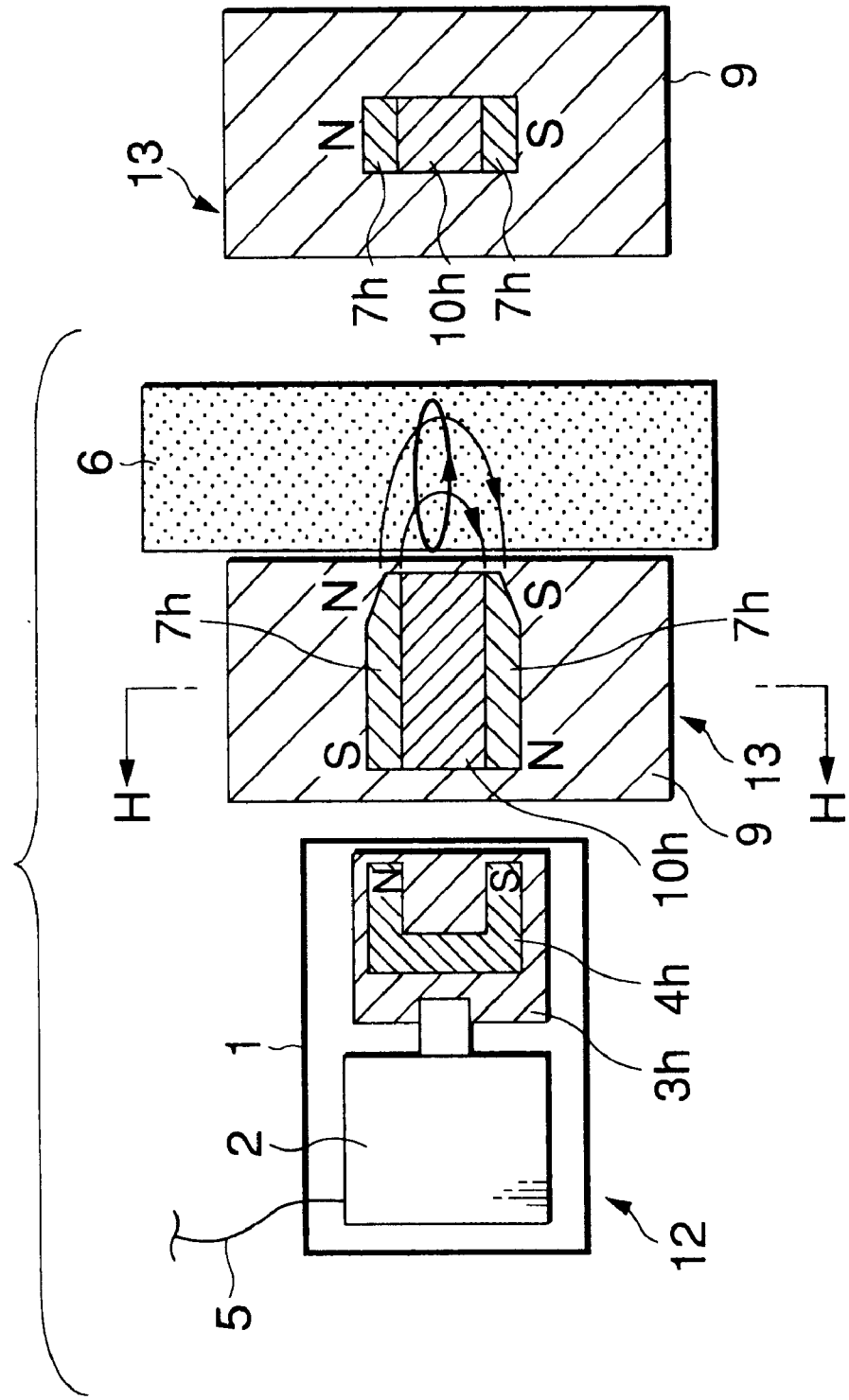

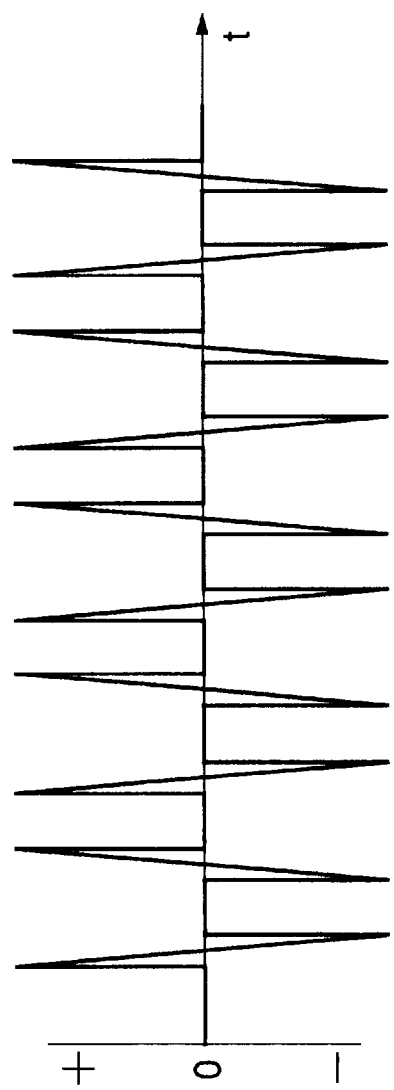

10Hz

20Hz

1ms

2ms

EDDY CURRENTS
DUE TO GENERATION
OF INDUCED
ELECTROMOTIVE
FORCE e

EDDY CURRENTS DUE TO GENERATION OF INDUCED ELECTROMOTIVE FORCE e

EDDY CURRENTS
DUE TO GENERATION
OF INDUCED
ELECTROMOTIVE
FORCE e

EDDY CURRENTS
DUE TO GENERATION
OF INDUCED
ELECTROMOTIVE
FORCE e

MAGNETIC STIMULATING APPARATUS FOR A LIVING BODY

BACKGROUND OF THE INVENTION

1. Field of the Invention

The invention relates to a magnetic stimulating apparatus which applies a magnetic field to a living body to generate eddy currents to treat health disorders such as, urinary incontinence.

2. Related Art

For example, the treatment of urinary incontinence based on magnetism is conducted in the following manner. A pulsative magnetic field of a magnetic flux density of 0.01 to 3 teslas, a repetitive frequency of about 1 to 100 Hz, and a pulse width of about 100 $\mu$s to 1 ms is continuously applied to the pudendum or the waist for about 15 minutes, thereby generating eddy currents.

As described in Examined Japanese patent publication HEI 3-67423, for example, such a magnetic field is generated by repeatedly supplying a pulsative large current to a coil.

A pulsative magnetic field due to a coil is generated by applying a DC voltage V to a capacitor to store charges, switching a thyristor to convert the energy $W_1 = CV^2/2$ (where C is the capacitance of the capacitor) stored in the capacitor into a pulse current, and by supplying the pulse current to the coil. In order to generate a large pulsative magnetic field, therefore, countermeasures: (1) C and V are increased; and (2) the inductance L of the coil is increased must be taken.

When the inductance L of a coil is increased, however, also the resistance R of the coil is increased, with the result that a large amount of heat $W_2 = i^2 R/2$ is generated by a large current i and the increased resistance R. In this way, in the method in which a magnetic field for stimulating a living body is generated from a coil, most of the supplied energy is dissipated as heat, resulting in a large power loss. In the method, therefore, the efficiency of generating a magnetic field is poor and a large power (several hundreds watts) is required. The generated heat is not used in the treatment. During the treatment which is continuously conducted for about 15 minutes, such heat may cause burn or impede the stable operation of the apparatus. In the case of the treatment of stress incontinence, particularly, since a high repetitive frequency (50 Hz) must be used, the heat loss is large. As a result, a large amount of energy must be replenished and hence continuous stimulation is hardly conducted by using a usual commercial power source.

When magnetism is to be generated for a long period by the method, a large cooling equipment is inevitably required, resulting in that the whole size of the apparatus is greatly enlarged. Such an apparatus occupies a large space in a treatment room, so that works for treatment is impeded. In the method, furthermore, the capacitor and the coil are bulk and large currents are supplied to them. Therefore, loud noises are produced in a treatment room by vibration of the capacitor or the coil.

SUMMARY OF THE INVENTION

The invention has been conducted in view of such defects of the prior art. It is an object of the invention to provide an apparatus which does not generate beat and which is quiet.

There is provided an apparatus of the present invention including: a permanent magnet which applies a magnetic field to a living body; and a magnet moving unit which moves said permanent magnet for a living body with respect to said living body.

The apparatus of the present invention is configured so that, in the apparatus set forth in claim 1, said apparatus further comprises a magnetic member which is attached to at least one of poles of said permanent magnet and which is high in magnetic permeability and saturation magnetization.

In one embodiment, the apparatus of the present invention is configured so that a portion of said magnetic member which is directed to the living body has a shape of a section area which is reduced as moving toward a tip end face.

In another embodiment, the apparatus is configured so that the apparatus comprises at least one pair of permanent magnets, and said pair of permanent magnets are disposed in a state where poles of the same kind of said pair of permanent magnets are close to each other.

In another embodiment, the apparatus is configured so that said apparatus further comprises a diamagnetic member which is adjacent to said permanent magnet and which guides a direction of magnetic fluxes generated from said permanent magnet for in a predetermined direction.

The apparatus of the present invention is configured so that said magnet moving unit is rotating means for rotating said permanent magnet.

The apparatus of the present invention is configured so that said rotating means comprises: a magnet holding member which holds said permanent magnet; and a motor which rotates said magnet holding member.

The apparatus of the present invention is configured so that said magnet moving unit is a reciprocating means for reciprocating said permanent magnet.

The apparatus of the present invention is configured so that said reciprocating means comprises: a magnet holding member to which said permanent magnet is attached; a conductive coil which is attached to said magnet holding member; a power source circuit which supplies to said coil a current which periodically changes; and a permanent magnet for a coil which applies a magnetic field to said coil.

The apparatus of the present invention is configured so that said reciprocating means comprises: a magnet holding member to which said permanent magnet is attached; a guide unit which guides said magnet holding member so as to reciprocate in predetermined directions; a conductive coil which is disposed in the vicinity of said guide unit; and a power source circuit which supplies to said coil a current which periodically changes.

In another embodiment of the present invention the apparatus is configured so that said apparatus further comprises a moving mechanism unit which moves said magnet moving unit in a predetermined direction with respect to said support unit.

Another embodiment of the present invention comprises: variable magnetic field generating means which comprises: a permanent magnet which applies a magnetic field to a living body; and a magnet moving unit which is attached to said support unit and which moves said permanent magnet with respect to said support unit; and magnetic field transmitting means which is separated from said variable magnetic field generating means, which is disposed on or in a living body and which comprises a magnetic member which transmits a magnetic field to the living body.

Another embodiment of the present invention comprises: rotating member which is fixed to said support unit; and plural magnetic force generating members which respectively hold along a peripheral face different numbers of permanent magnets for applying a magnetic field to a living body, and which are detachable with respect to a rotation shaft of said rotating means.

Another embodiment of the present invention comprises: plural permanent magnets which apply a magnetic field to a living body; a magnet holding member which holds said permanent magnets along a peripheral face; and rotating means which is fixed to said support unit and to which said magnet holding member is attached via a rotation shaft, at least one of said permanent magnets being detachable with respect to said magnet holding member.

Another embodiment of the present invention comprises: rotating means which is fixed to said support unit; and plural magnetic force generating members which respectively hold along a peripheral face permanent magnets for applying a magnetic field to a living body, and which are detachable with respect to a rotation shaft of said rotating means, said permanent magnets held by each of said magnetic force generating members being different in size from said permanent magnets held by the other magnetic force generating members.

Another embodiment of the present invention comprises: plural permanent magnets which apply a magnetic field to a living body and which are different from each other in size; a magnet holding member which detachably holds at least one of said permanent magnets along a peripheral face; and rotating means which is fixed to said support unit and to which said magnet holding member is attached via a rotation shaft.

BRIEF DESCRIPTION OF THE DRAWINGS

FIGS. 1(a) and 1(b) are views showing the whole configuration of a first embodiment;

FIG. 2 is a view showing magnetic flux densities at points which are separated from a permanent magnet in a given direction;

FIG. 3 is a view showing a timing when a permanent magnet approaches a certain point in the living body, variation of the magnetic flux density B at the point, and eddy currents generated in the living body;

FIG. 13 is a view showing the level of eddy currents generated in the living body according to the sixth embodiment;

FIGS. 15(a) and 15(b) are views showing comparisons of eddy currents generated in the living body according to the seventh embodiment (having diamagnetic members) and the second embodiment (not having a diamagnetic member);

FIGS. 16(a) and 16(b) are views showing the whole configuration of an eighth embodiment;

FIG. 17 is a view showing the level of eddy currents generated in the living body according to the eighth embodiment;

DETAILED DESCRIPTION OF THE PREFERRED EMBODIMENTS

Figure 4A:
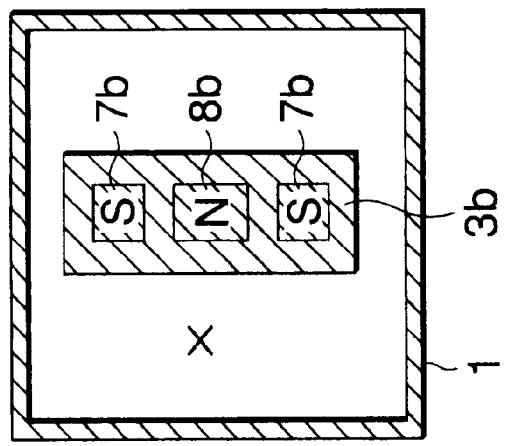
FIGS. 4(a) and 4(b) are views showing the whole configuration of a second embodiment.

Embodiments described below are based on the common principle that, when a living body is assumed to be one conductor and a varying magnetic field is applied to the living body, eddy currents are generated in the living body in conformance to Faraday's law of electromagnetic induction.

Specifically, assuming that magnetic fluxes $\phi$ (webers) pass through an area S ($m^2$) delimited by a closed curve C and a voltage e (V) is induced in the closed path C surrounding the portion of the area S, the following expression is held:

$$e = -d\phi/dt$$

where $\phi = BS$ (B: magnetic flux density, webers/m$^2$=teslas).

This principle is characterized in that the varying magnetic field is generated by moving a permanent magnet disposed in close proximity to the living body. Even when a varying magnetic field is generated by using a permanent magnet in this way, eddy currents are generated in the living body in the same manner as in the prior art apparatus for generating a varying magnetic field which uses a coil.

FIG. 1 is a view showing the configuration of a first embodiment, FIG. 1(a) is a partially cutaway side view, and FIG. 1(b) is a section view taken along the line A—A of FIG. 1(a). As shown in the figure, a motor 2 is housed in a plastic case 1 and fixed to the case 1. A magnet holding member 3a which is made of plastic and has drum-like shape is attached to the rotation shaft of the motor 2. A permanent magnet 4a is embedded in the magnet holding member 3a.

As the material of the permanent magnet 4a, rear earth cobalt, alnico, ferrite, or the like may be used. Preferably, a material which can attain a magnetic flux density as high as possible is selected. The permanent magnet 4a is placed so that one end of the magnet is flush with the peripheral face of the magnet holding member 3a. The motor 2 is connected to a control unit and a power source circuit which are disposed outside the apparatus and not shown, via a cord 5. The control unit controls the rotational speed of the motor 2. Namely, the control unit controls the motor 2 so that the motor rotates at a speed which is set by the operator. In the embodiment, the case 1 serves as the support unit which is supported from an outside, and the motor 2, the control unit, and the power source circuit constitute the rotating means.

When the apparatus is to be used, the operator adjusts the control unit so as to set the rotational speed of the motor 2. Next, the operator turns on a switch of the power source circuit and causes the apparatus to contact the surface of a living body (the body of the patient) 6 while holding the apparatus with a hand. At this time, the permanent magnet 4a rotates. In the region of the living body 6 elongating along the orbit of the magnet, therefore, the magnetic field periodically varies and eddy currents are generated, thereby treating the patient.

As shown in FIG. 2, the magnetic flux density B in the living body 6 is lower as the distance Z between the surface of the living body and the permanent magnet is larger. Consequently, the magnetic flux density B is adjusted by changing the distance Z.

In the treatment of urinary incontinence, usually, the pulsative magnetic field applied to the living body has a pulse width of 100 μs to 1 ms. The pulse width depends on the rotational speed of the magnet holding member 3a, the radius R of the magnet holding member 3a, and the width W of the permanent magnet. When the rotational speed of the motor 2 is 1,200 rpm (i.e., the frequency f=20 Hz), for example, the pulse width ΔT in the region of the living body 6 elongating along the peripheral face of the magnet holding member 3a (in the case where the length L of the permanent magnet 4a is sufficiently larger than the radius of the magnet holding member 3a, the region where the permanent magnet 4a passes over) can be indicated by the following expression:

$$\Delta T(\text{ms}) = \{1{,}000(\text{ms})/20\} \cdot (W/2\pi R) \tag{1}$$

In order to reduce the pulse width ΔT, the radius R of the magnet holding member 3a must be increased. FIG. 3 shows the timing of the generation of the pulsative magnetic field in the above-mentioned region of the living body 6, the variation of the magnetic flux density B, and eddy currents due to the generation of an induced electromotive force e in the case where the rotational speed of the motor 2 is 1,200 rpm (the frequency f=20 Hz).

Figure 4B:
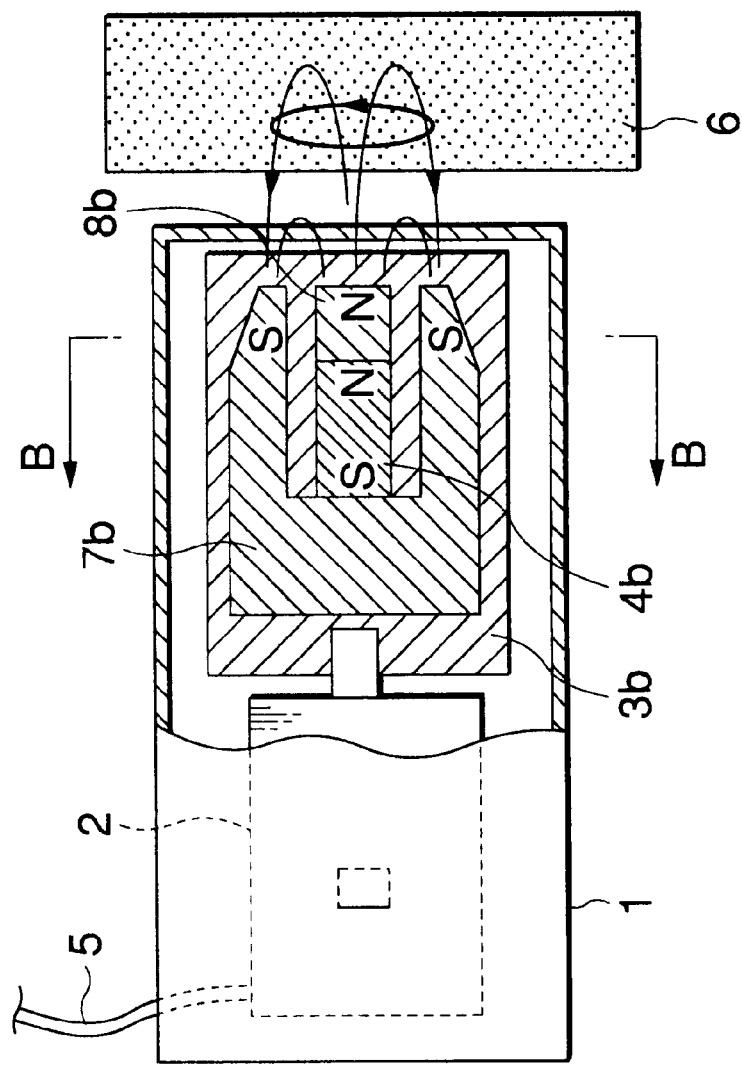

FIG. 4 shows the configuration of a second embodiment, FIG. 4(a) is a partially cutaway side view, and FIG. 4(b) is a section view taken along the line B–B of FIG. 4(a). The embodiment is different from the first embodiment in that a magnetic member 7b is joined to one pole of a permanent magnet 4b and a magnetic member 8b is joined to the other pole of the permanent magnet 4b. A magnet holding member 3b which is made of plastic is molded integrally with the magnetic members 7b and 8b and the permanent magnet 4b under the state where the members 7b and 8b and the permanent magnet are incorporated in the magnet holding member. The magnet holding member 3b is attached to the shaft of the motor 2. The magnetic member 7b has two projections which elongate toward the side opposed to the living body 6, so as to sandwich the permanent magnet 4b. In each of the projections, a portion of a predetermined length has a shape which is gradually thinned as it extends toward the tip end face. Both the magnetic members 7b and 8b are high in magnetic permeability and saturation magnetization. The other components are configured in the same manner as those of the first embodiment and hence designated by the same reference numerals.

Also in the embodiment, the rotation of the motor 2 causes the permanent magnet 4b to rotate, and a varying magnetic field is generated in the living body 6 by the magnetic members 7b and 8b, thereby generating eddy currents.

In the embodiment, the magnetic members 7b and 8b which have a high magnetic permeability and a high saturation magnetization are joined to the permanent magnet 4b, and the portions opposed to the living body 6 have a tapered shape. As compared with the first embodiment, therefore, magnetic fluxes are concentrated so as to increase the magnetic flux density, and the total number of magnetic fluxes entering the living body is increased, with the result that also the level of eddy currents is increased.

Figure 5:
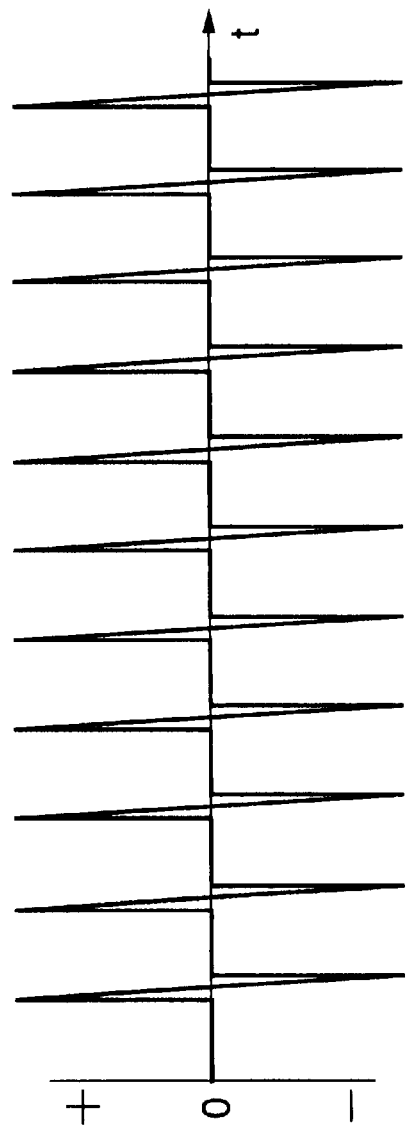
FIG. 5 is a view showing the level of eddy currents generated in the living body according to the second embodiment.

FIG. 5 shows eddy currents in the living body due to the generation of an induced electromotive force e according to second embodiment.

FIG. 4(a) shows an example of eddy currents at a position which is deviated from an extension line of the rotation center of the permanent magnet 4b (in FIG. 4(b), for example, the position in the living body 6 which corresponds to the position indicated by the symbol X).

Figure 6:
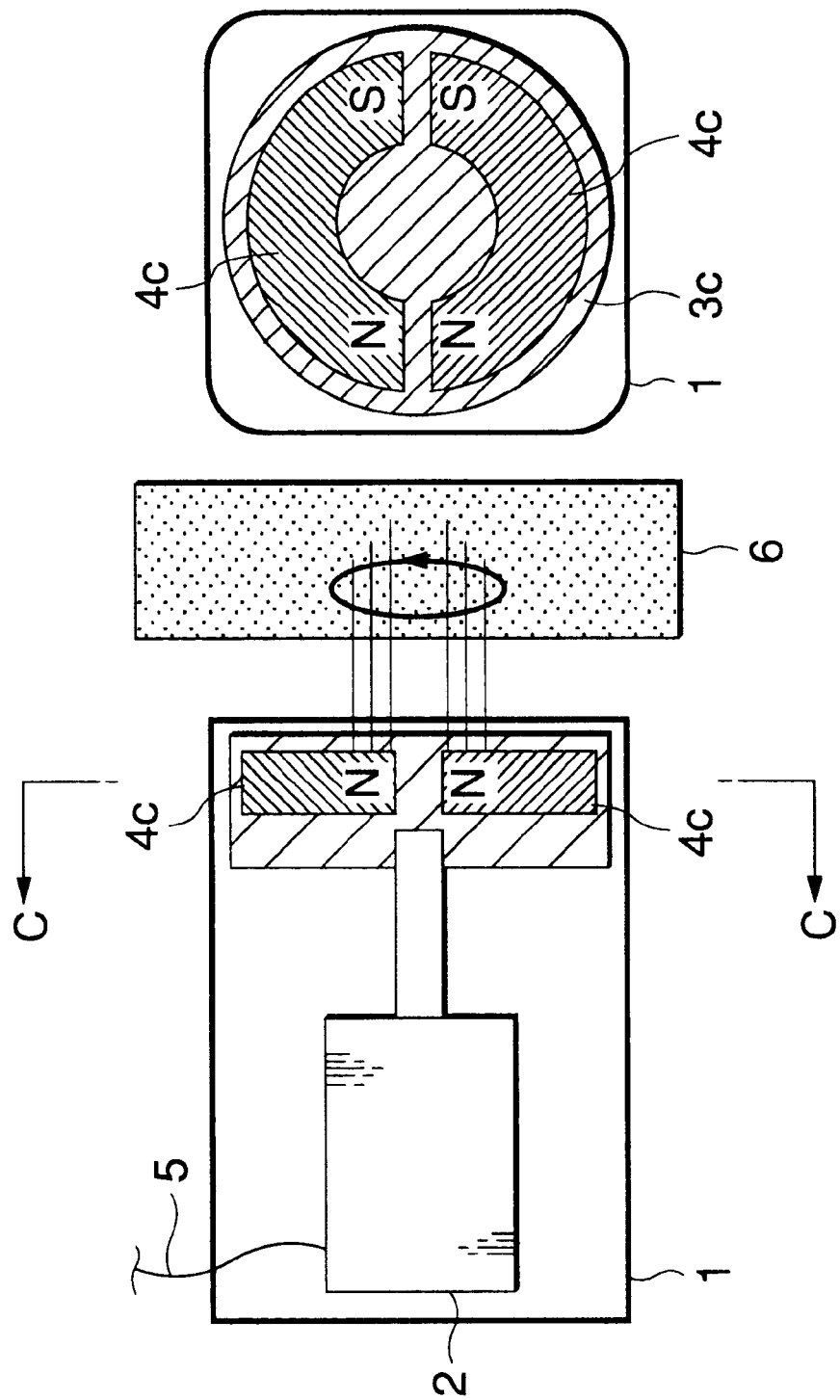
FIGS. 6(a) and 6(b) are views showing the whole configuration of a third embodiment.

FIG. 6 shows the configuration of a third embodiment, FIG. 6(a) is a side section view, and FIG. 6(b) is a section view taken along the line C–C of FIG. 6(a). The embodiment is different from the first embodiment in that one pair of permanent magnets 4c are used and the permanent magnets are disposed so that the N-poles of the magnets are opposed to each other and the S-poles are opposed to each other. Each of the permanent magnets 4c has a shape which is curved so as to form a semicircular arc. The permanent magnets are held by a magnet holding member 3c, and disposed so as to surround the rotation center of the member. The magnet holding member 3c is made of plastic and molded integrally with the pair of permanent magnets 4c under the state where the permanent magnets are incorporated in the magnet holding member. The magnet holding member 3c is attached to the shaft of the motor 2. The other components are configured in the same manner as those of the first embodiment and hence designated by the same reference numerals.

Also in the embodiment, the rotation of the motor 2 causes the permanent magnets 4c to rotate and a varying magnetic field is generated in the living body 6, thereby generating eddy currents.

In the embodiment, the N-poles of the permanent magnets 4c repel each other so as to promote the advancement of the magnetic fluxes to the S-poles, with the result that the magnetic flux density between the N-poles and the total magnetic fluxes are increased. This causes the pulse width of the eddy currents to be increased, so that also the stimulation applied to the living body is increased. This is applicable also to the S-poles.

In the embodiment, a portion in which the magnetic flux density is high exists in two places, and hence the frequency is two times that of the case where such a portion exists in only one place. In the living body, eddy currents in the case where the N-pole is close to the desired portion of the living body to which stimulation is applied is opposite in direction to those in the case where the S-poles are close to the living body.

Figure 7:
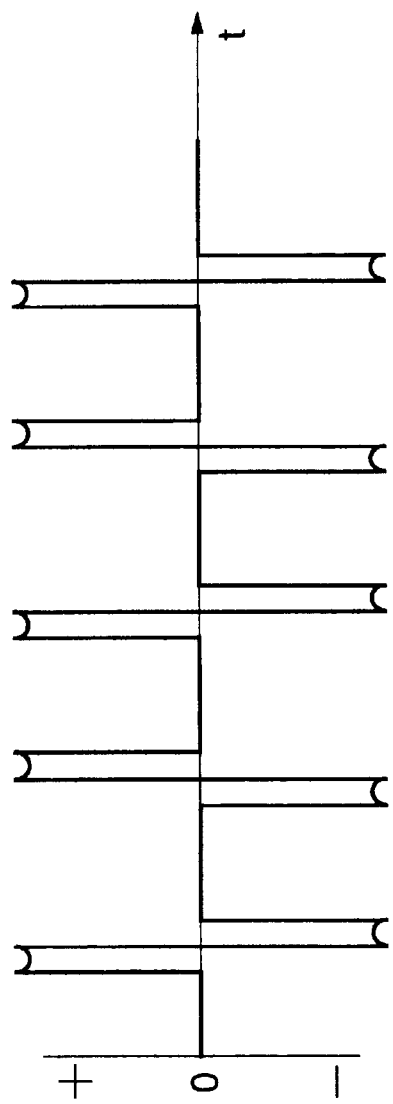
FIG. 7 is a view showing the level of eddy currents generated in the living body according to the third embodiment.

FIG. 7 shows eddy currents in the living body due to the generation of an induced electromotive force e according to third embodiment.

In the same manner as the second embodiment, FIG. 6(a) shows an example of eddy currents at a position which is deviated from an extension line of the rotation center of the permanent magnets 4c.

Figure 8:
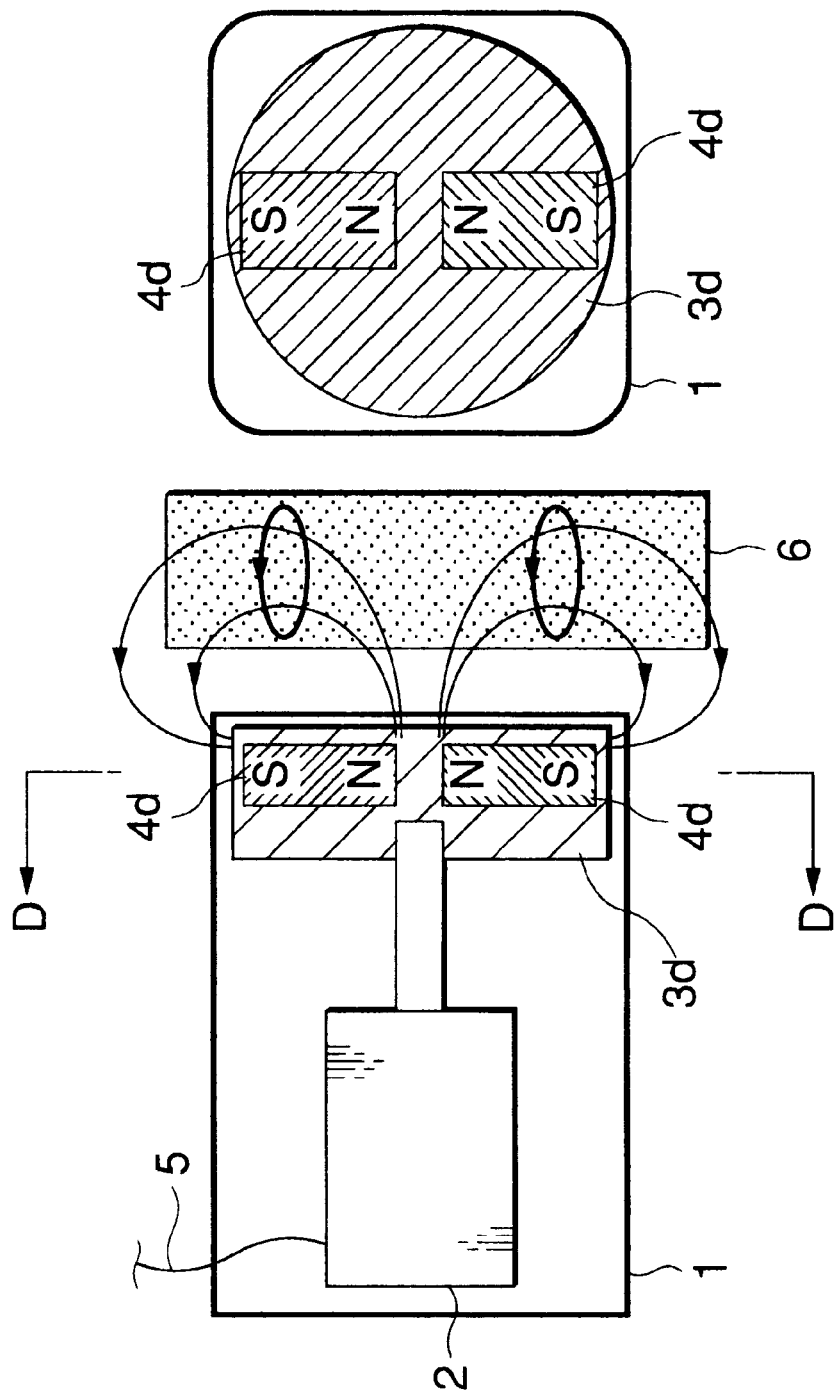
FIGS. 8(a) and 8(b) are views showing the whole configuration of a fourth embodiment.

FIG. 8 shows the configuration of a fourth embodiment, FIG. 8(a) is a side section view, and FIG. 8(b) is a section view taken along the line D—D of FIG. 8(a). In the embodiment, one pair of permanent magnets 4d are used in the same manner as the third embodiment. The permanent magnets are disposed so that poles of the same kind (the N-poles or the S-poles) are opposed to each other. The permanent magnets 4d have a rod-like shape and are held by a magnet holding member 3d. The permanent magnets are disposed so as to face each other with the rotation center of the magnet holding member 3d therebetween, and elongate in a radial direction of the magnet holding member 3d. The magnet holding member 3d is made of plastic and molded integrally with the pair of permanent magnets 4d under the state where the permanent magnets are incorporated in the magnet holding member. The magnet holding member 3d is attached to the shaft of the motor 2. The other components are configured in the same manner as those of the third embodiment and hence designated by the same reference numerals.

Also in the embodiment, the rotation of the motor 2 causes the permanent magnets 4d to rotate and a varying magnetic field is generated in the living body 6, thereby generating eddy currents.

In the embodiment, the N-poles of the permanent magnets 4d repel each other so as to promote the advancement of the magnetic fluxes to the S-poles, with the result that the magnetic flux density between the N-poles and the total magnetic fluxes are increased. This causes the pulse width of the eddy currents to be increased, so that also the stimulation applied to the living body is increased. This is applicable also to the S-poles.

In the embodiment, a portion in which the magnetic flux density is high exists in two places, and hence the frequency is two times that of the case where such a portion exists in only one place.

Figure 9:
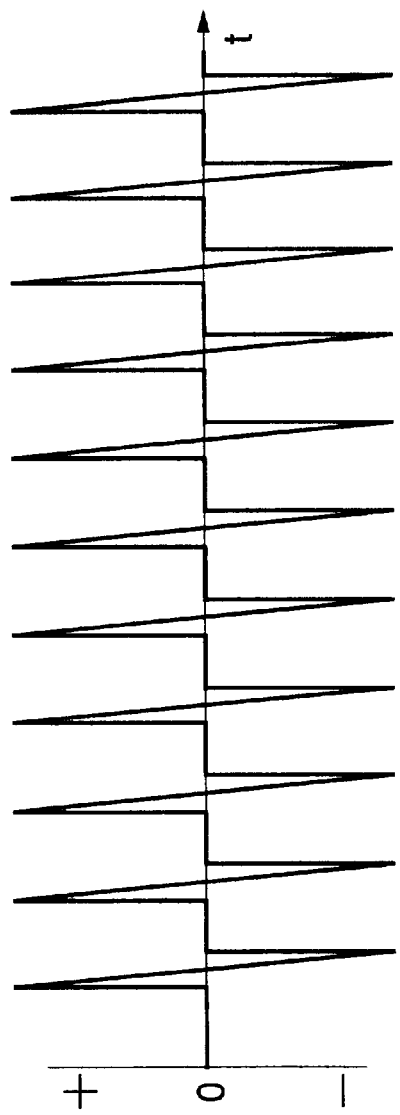
FIG. 9 is a view showing the level of eddy currents generated in the living body according to the fourth embodiment.

FIG. 9 shows eddy currents in the living body due to the generation of an induced electromotive force e according to fourth embodiment.

Figures 10A, 10B:
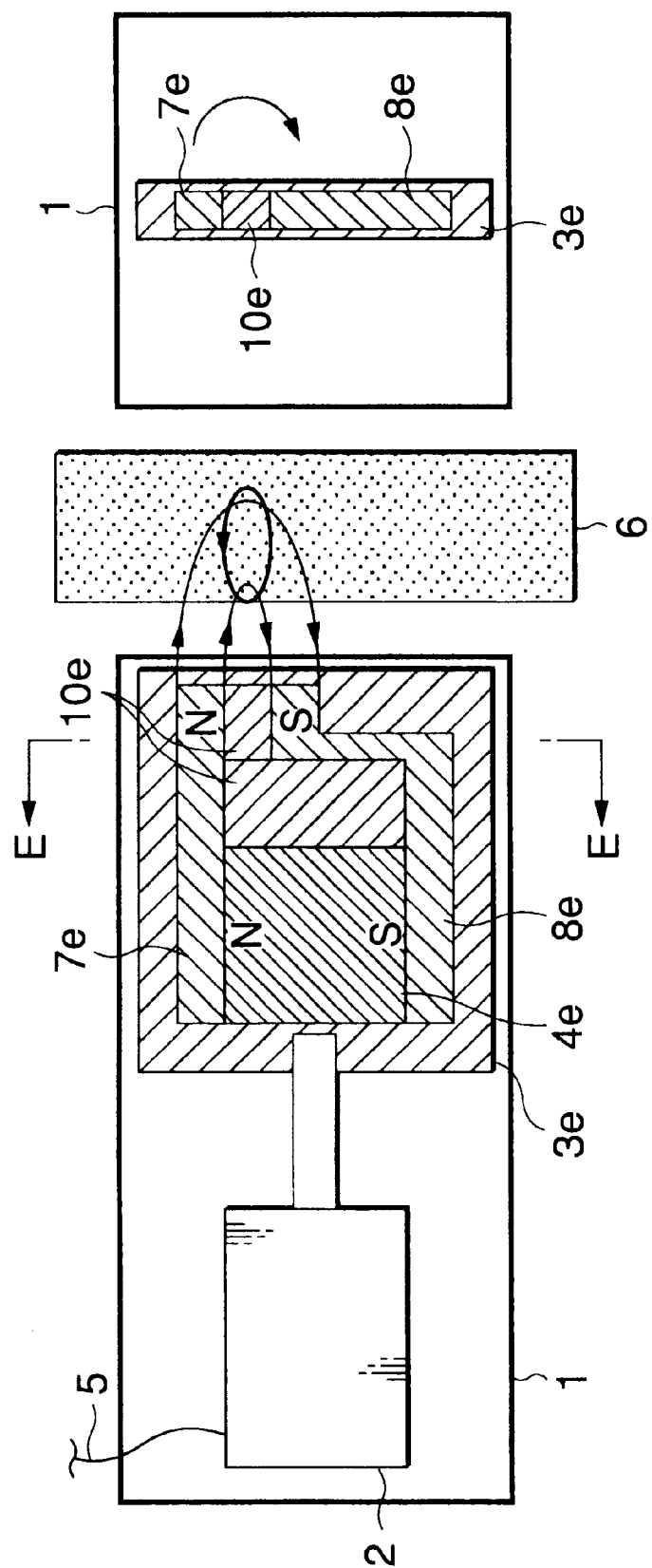
FIGS. 10(a) and 10(b) are views showing the whole configuration of a fifth embodiment.

FIG. 10 shows the configuration of a fifth embodiment, FIG. 10(a) is a side section view, and FIG. 10(b) is a section view taken along the line E—E of FIG. 10(a). In the embodiment, magnetic members 7e and 8e abut against the N- and S-poles of a permanent magnet 4e, respectively, the tip ends of the magnetic members 7e and 8e are projected in a state where they are close to each other, and disposed so as to be directed toward the living body 6, and the areas of the tip end faces of the members are smaller than those of the tip end faces of the N- and S-poles of the permanent magnet 4e. The magnetic members 7e and 8e are made of a ferromagnetic material which has a high magnetic permeability and a high saturation magnetization. In the embodiment, furthermore, a diamagnetic member 10e is disposed between the magnetic members 7e and 8e. The magnet 4e and the magnetic members 7e and 8e are held by a magnet holding member 3e. The magnet holding member 3e is made of plastic and molded integrally with the permanent magnet 4e and the magnetic members 7e and 8e under the state where the permanent magnet and the magnetic members are incorporated in the magnet holding member. The magnet holding member 3e is attached to the shaft of the motor 2. The gap between the tip ends of the magnetic members 7e and 8e is deviated from the rotation center of the magnet holding member 3e. The magnetic members 7e and 8e are made of a magnetic material which has a high magnetic permeability and a high saturation magnetization. The other components are configured in the same manner as those of the first embodiment and hence designated by the same reference numerals.

Also in the embodiment, the rotation of the motor 2 causes the permanent magnet 4e and the magnetic members 7e and 8e to rotate and a varying magnetic field is generated in the living body 6, thereby generating eddy currents.

In the embodiment, magnetic fluxes generated from the permanent magnet 4e are concentrated in the tip ends of the magnetic members 7e and 8e having a small area, and hence the magnetic flux density in the living body 6 is increased, with the result that a large induced electromotive force is generated in the living body 6. In the embodiment, furthermore, since the diamagnetic member 10e is interposed between the magnetic members 7e and 8e, it is possible to prevent lines of magnetic force from being generated along a short path from the N-pole to the S-pole. As a result, lines of magnetic force reach a deep position in the living body 6 and a large magnetic stimulation power, which is hardly obtained in the prior art, can be generated.

Figure 11:
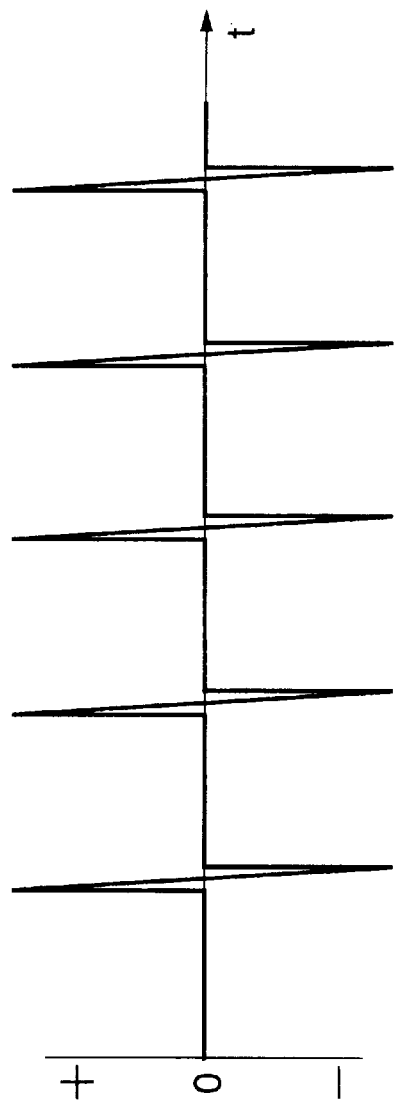
FIG. 11 is a view showing the level of eddy currents generated in the living body according to the fifth embodiment.

FIG. 11 shows eddy currents in the living body due to the generation of an induced electromotive force e according to fifth embodiment.

Figures 12A, 12B:
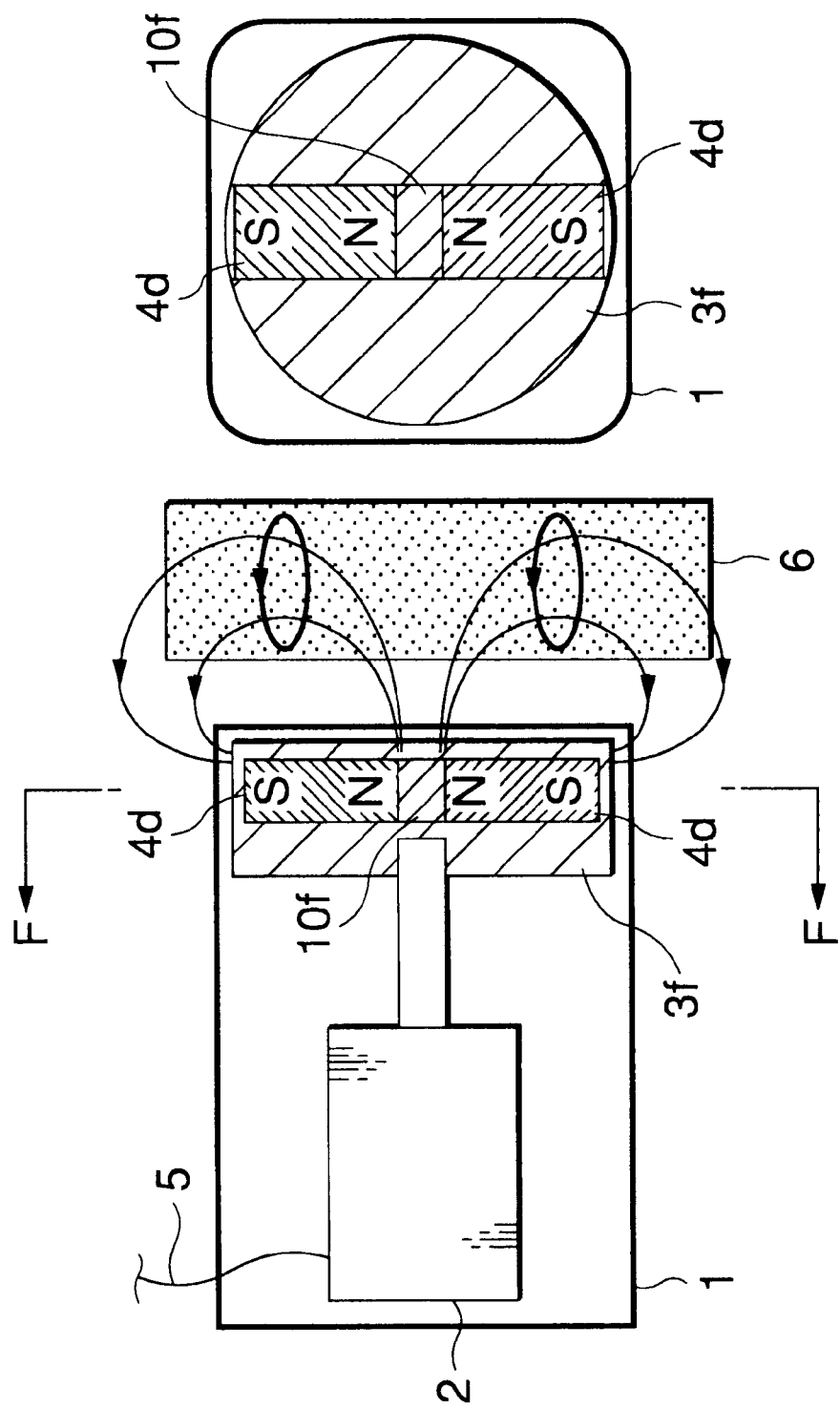
FIGS. 12(a) and 12(b) are views showing the whole configuration of a sixth embodiment.

FIG. 12 shows the configuration of a sixth embodiment, FIG. 12(a) is a side section view, and FIG. 12(b) is a section view taken along the line F—F of FIG. 12(a). The embodiment is obtained by modifying the fourth embodiment shown in FIG. 8 so that a diamagnetic member 10f is disposed between the two permanent magnets 4d. The diamagnetic member and permanent magnets are held by a magnet holding member 3f. The other components are configured in the same manner as those of the fourth embodiment and hence designated by the same reference numerals.

Also in the embodiment, the rotation of the motor 2 causes the permanent magnets 4d to rotate and a varying magnetic field is generated in the living body 6, thereby generating eddy currents.

In the embodiment, as compared with the fourth embodiment, the existence of the diamagnetic member 10f allows magnetic fluxes to be concentrated, and hence the magnetic flux density and the total magnetic fluxes in the living body are increased. As a result, also eddy currents are increased.

FIG. 13 shows eddy currents in the living body due to the generation of an induced electromotive force e according to sixth embodiment.

Figure 14B:
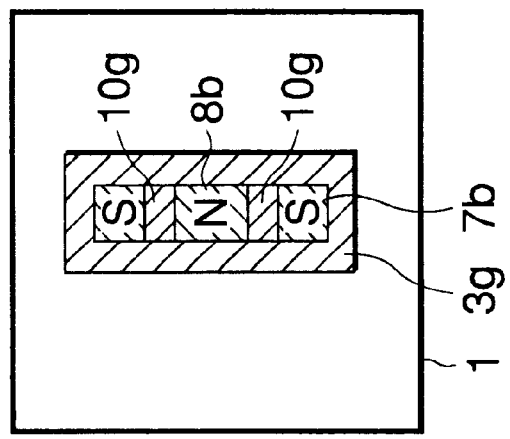
FIGS. 14(a) and 14(b) are views showing the whole configuration of a seventh embodiment.
Figure 14A:
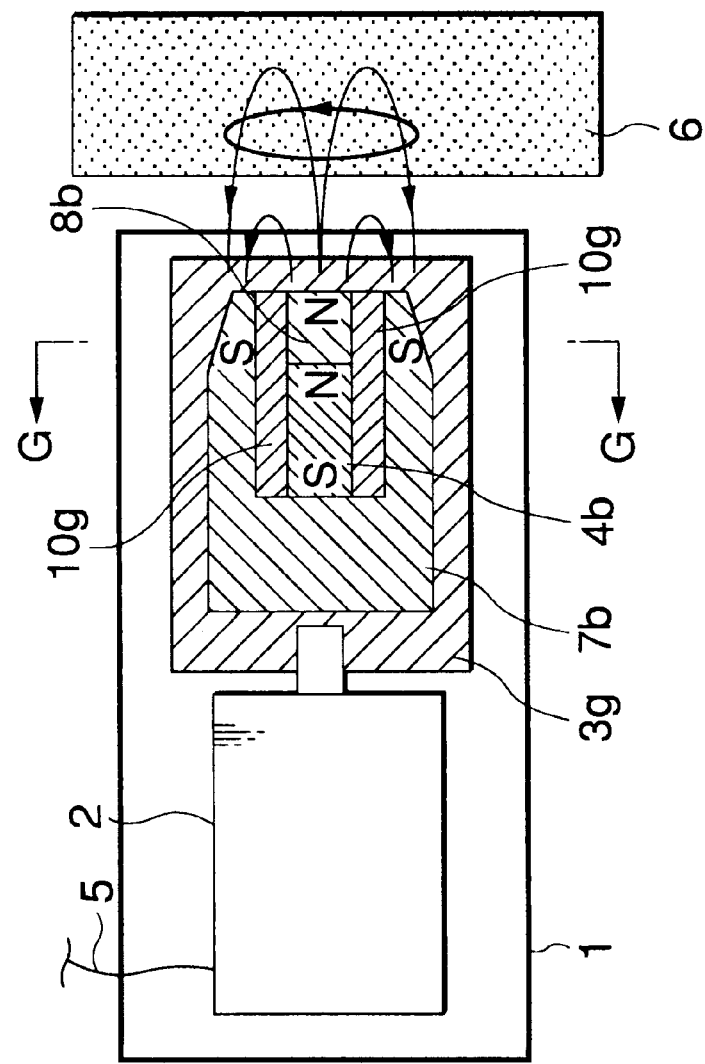

FIG. 14 shows the configuration of a seventh embodiment, FIG. 14(a) is a side section view, and FIG. 14(b) is a section view taken along the line G—G of FIG. 14(a). The embodiment is obtained by modifying the second embodiment shown in FIG. 4 so that diamagnetic members 10g are disposed between the permanent magnet 4b and the magnetic members 7b and 8b. These members and magnet are held by a magnet holding member 3g. The other components are configured in the same manner as those of the second embodiment and hence designated by the same reference numerals.

Also in the embodiment, the rotation of the motor 2 causes the permanent magnet 4b and the magnetic members 7b and 8b to rotate and a varying magnetic field is generated in the living body 6, thereby generating eddy currents.

In the embodiment, as compared with the second embodiment, the existence of the diamagnetic members 10g allows magnetic fluxes to be concentrated, and hence the magnetic flux density and the total magnetic fluxes in the living body are increased. As a result, also eddy currents are increased.

With respect to the embodiment (in which diamagnetic members are disposed) and the second embodiment (in which no diamagnetic member is disposed), FIG. 15 shows the timing at which the permanent magnet approaches the living body, the variation of the magnetic flux density B in the surface of the living body, and eddy currents due to the generation of an induced electromotive force e. As shown in the figure, the magnetic flux density B and the induced electromotive force e according to embodiment are larger than those of the second embodiment.

FIG. 16 shows the configuration of an eighth embodiment, FIG. 16(a) is a side section view, and FIG. 16(b) is a section view taken along the line H—H of FIG. 16(a). The apparatus is configured by a permanent-magnet rotating unit 12 (variable magnetic field generating means) and a nonrotational magnetic member unit 13 (magnetic field transmitting means). The permanent-magnet rotating unit 12 comprises: a permanent magnet 4h; a permanent-magnet holding unit 3h which holds the permanent magnet 4h; a motor 2 which rotates the permanent-magnet holding unit 3h; and a plastic case 1 to which the motor 2 is fixed and which houses these components. The motor 2 is connected to a control unit and a power source circuit which are disposed outside the apparatus, via a cord 5. The nonrotational magnetic member unit 13 is separated from the permanent-magnet rotating unit 12, and comprises: a pair of magnetic members 7h; a diamagnetic member 10h which is disposed between the magnetic members; and a holding member 9 which integrally holds these members and which is made of plastic. The nonrotational magnetic member unit is to be fixed to the living body 6. The pair of magnetic members 7h are made of a magnetic material which has a high magnetic permeability and a high saturation magnetization.

In the embodiment, the nonrotational magnetic member unit 13 (the magnetic members 7b) which is to be fixed to the living body 6 is not rotated. The magnetic field is transmitted from the permanent magnet 4h which is rotated by the motor 2 to the magnetic members 7h. Each time when the permanent magnet 4h is rotated, magnetic fields in which the N- and S-poles are changed are alternatingly transmitted. Eddy currents flow in the living body on each transmission.

The embodiment is configured by the permanent-magnet rotating unit 12 and the nonrotational magnetic member unit 13. In a region of the living body 6 which the permanent-magnet rotating unit 12 cannot approach because of its large size, therefore, the nonrotational magnetic member unit 13 is fixed to the living body and eddy currents are generated in the living body via the member unit. For example, the nonrotational magnetic member unit 13 is inserted into the anus, and a magnetic field is applied to the living body 6 by the permanent-magnet rotating unit 12 from the outside of the living body, whereby eddy current can be generated.

FIG. 17 shows eddy currents in the living body due to the generation of an induced electromotive force e according to eighth embodiment.

Figure 18A:
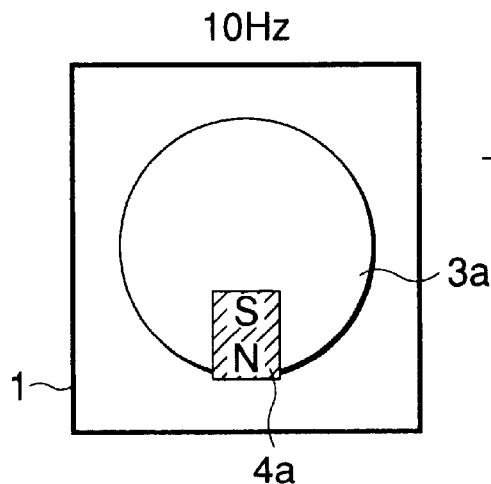
FIGS. 18(a) and 18(b) are views illustrating a ninth embodiment.
Figure 18B:
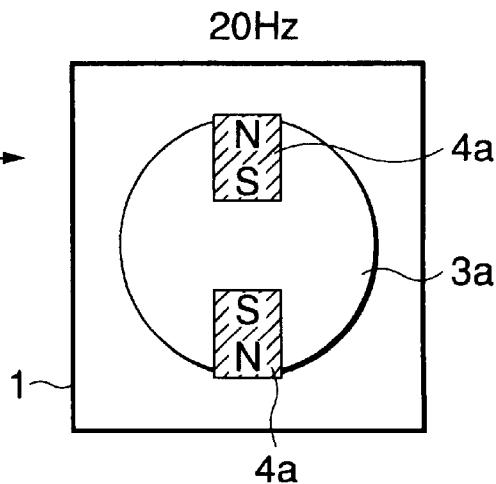

A ninth embodiment will be described. The embodiment is substantially identical with the first embodiment shown in FIG. 1 but different in the following point. The embodiment uses two kinds of magnetic force generating members each of which comprises a permanent magnet 4a and a magnet holding member 3a such as shown in FIG. 1 and which can be easily attached to and detached from the rotation shaft of the motor 2 by means of screws. In one of the magnetic force generating members, one permanent magnet 4a is attached to the magnet holding member 3a as shown in FIG. 18(a), i.e., in the same manner as the first embodiment. In the other magnetic force generating member, as shown in FIG. 18(b), two permanent magnets 4a are attached so as to be symmetrical about the center of the magnet holding member 3a. The case 1 has an opening and a lid which covers the opening, thereby enabling the operator to conduct replacement of the magnetic force generating member through the opening.

According to the embodiment ninth, even when the rotational rate of the motor 2 is not changed, the frequency of the pulsative magnetic field applied to the living body can be changed by replacing the magnetic force generating member with the other one. It is assumed that the rotational rate of the motor 2 is 600 rpm. When the magnetic force generating member shown in FIG. 18(a) is used, the frequency of the pulsative magnetic field applied to the living body is 10 HZ. By contrast, when the magnetic force generating member shown in FIG. 18(b) is used, the frequency is 20 HZ. In this example, two kinds of magnetic force generating members are used. However, the number of the kinds of magnetic force generating members comprising permanent magnets of different numbers is not restricted.

A tenth embodiment will be described. In the ninth embodiment, the magnetic force generating members each comprising the permanent magnet 4a and the magnet holding member 3a are replaced with each other. In the tenth embodiment, each magnetic force generating member comprises plural permanent magnets which are detachably attached to a single magnet holding member. According to this configuration, the operator can attach a required number of permanent magnets to the magnet holding member, and it is possible to attain the effect same as that of the ninth embodiment.

An eleventh embodiment will be described. In the ninth embodiment, the plural magnetic force generating members comprise permanent magnets of different numbers. In eleventh embodiment, plural magnetic force generating members comprise permanent magnets of different widths. The other components are configured in the same manner as those of the ninth embodiment.

Figure 19A:
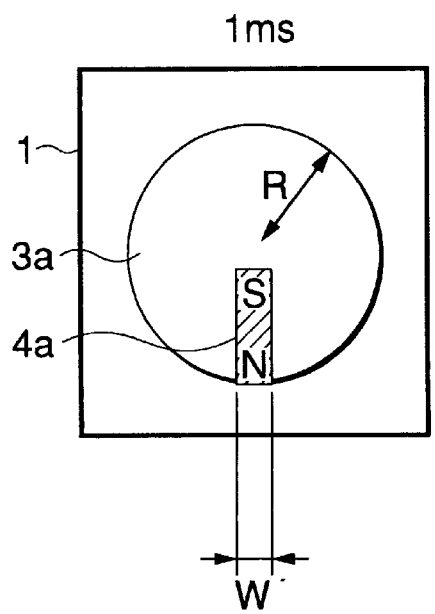
FIGS. 19(a) and 19(b) are views illustrating an eleventh embodiment.
Figure 19B:
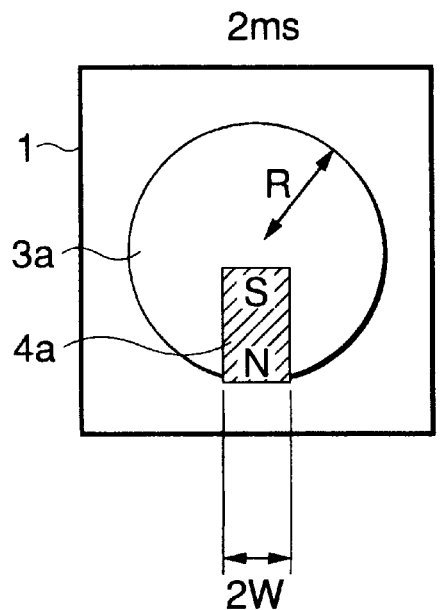

According to the eleventh embodiment, the pulse width of the pulsative magnetic field applied to the living body can be changed by using different permanent magnets. In a magnetic force generating member shown in FIG. 19(a), for example, the permanent magnet 4a has a width of W and the pulse width is 1 ms at a certain rotational speed. In a magnetic force generating member shown in FIG. 19(b), the permanent magnet 4a has a width of 2W and hence the pulse width is 2 ms at the same rotational speed. In this example, two kinds of magnetic force generating members are used. However, the number of the kinds of magnetic force generating members comprising the permanent magnets 4a of different widths is not restricted.

A twelfth embodiment will be described. In the eleventh embodiment, the plural magnetic force generating member comprising the permanent magnet and the magnet holding member is replaced with another one. In the fifteenth embodiment, plural permanent magnets of different widths are used, and one of the permanent magnets is detachably attached to a single magnet holding member. According to this configuration, the operator can attach a permanent magnet of a required width to the magnet holding member, and it is possible to attain the effect same as that of the eleventh embodiment.

Figure 20:
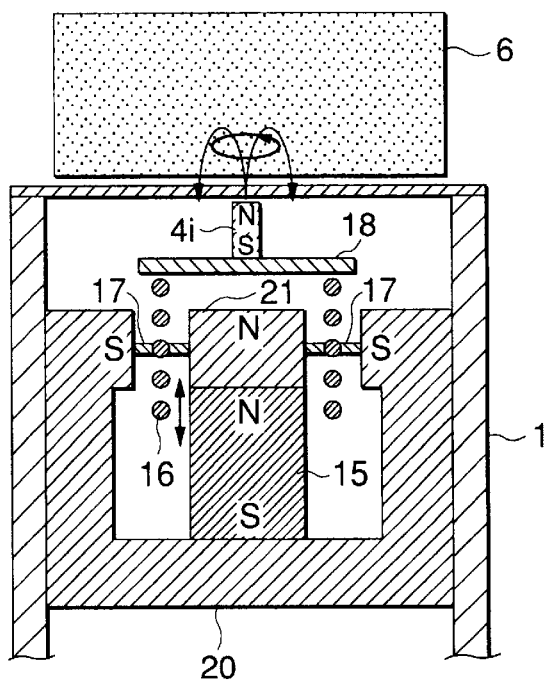
FIG. 20 is a view showing the configuration of a thirteenth embodiment.

A thirteenth embodiment will be described. In the embodiment, a permanent magnet for a living body which applies a magnetic field to the living body is moved by the principle same as that of a loudspeaker. FIG. 20 is a side section view of the embodiment. Magnetic members 20 and 21 are joined to the poles of a permanent magnet 15, respectively. The one magnetic member 20 has two projections which elongate in parallel with the side faces of the permanent magnet 15. The tip end faces of the projections are opposed to a side face of the other magnetic member 21. A coil 16 which is made of copper is inserted between the magnetic members 20 and 21, with being centered with respect to the permanent magnet 15 and the magnetic member 21. The magnetic members 20 and 21 are made of a magnetic material which has a high magnetic permeability and a high saturation magnetization.

The coil 16 is held between the magnetic members 20 and 21 by a pair of dampers 17 which are bonded at an end portion to the magnetic members 20 and 21, respectively. Each of the dampers 17 is formed by a flexible member such as rubber, cloth, or a flexible film. A plate-like member 18 which is made of plastic is attached to one end of the coil 16. A permanent magnet 4i for a living body which applies a magnetic field to the living body 6 is fixed to the outer surface of the plate-like member 18. The one magnetic member 20 which applies a magnetic field to the coil 16 is fixed to the plastic case 1. The above-mentioned components including the magnetic member 20 are housed in the case 1. A control unit and a power source circuit (both are not shown) which are used for supplying a pulse current are connected to the coil 16. The direction of the pulse current may be fixed to one direction, or alternatingly changed to two directions. The control unit controls the period of the pulse current. The period can be set by the operator. In the embodiment, the case 1 serves as the support unit which is supported from an outside, the plate-like member 18 serves as the magnet holding member which holds the permanent magnet 4i, and the coil 16, the dampers 17, the control unit, and the power source circuit constitute the reciprocating means.

In the thus configured apparatus, the operator adjusts the control unit to set the frequency of the pulse current, and then turns on the switch of the power source circuit. As a result, the pulse current is supplied to the coil 16, and the coil 16 vibrates in the directions of the arrows of FIG. 20 in accordance with Fleming's rule. Therefore, the plate-like member 18 vibrates, and also the permanent magnet 4i vibrates. As a result, magnetic fluxes in the living body 6 are changed so as to generate eddy currents.

The embodiment is very simple in structure. In the embodiment, when the permanent magnet 4i is made as light as possible, it rapidly moves, resulting in that larger eddy currents can be generated.

Figure 21:
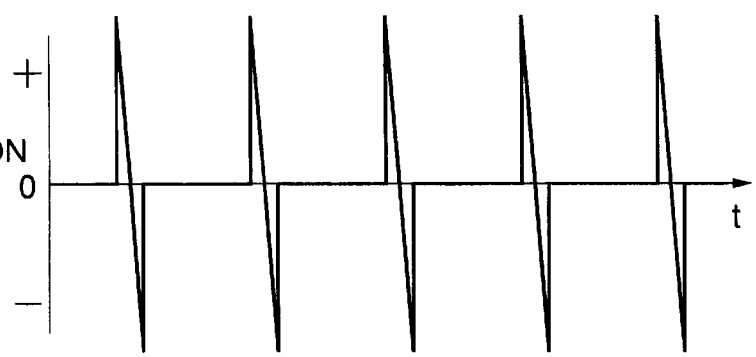
FIG. 21 is a view showing the level of eddy currents generated in the living body according to the thirteenth embodiment.

FIG. 21 shows eddy currents in the living body due to the generation of an induced electromotive force e according to thirteenth embodiment.

Figure 22:
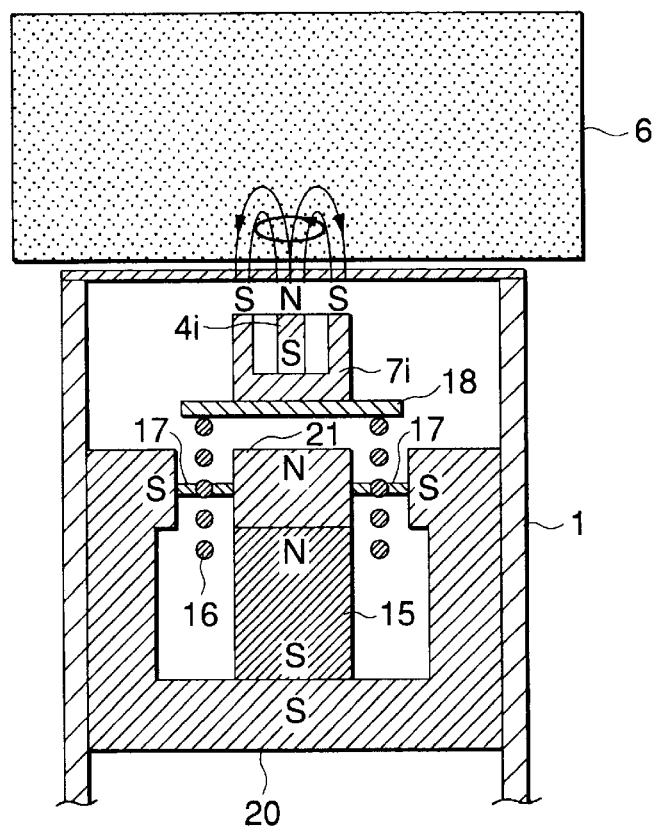
FIG. 22 is a view showing the configuration of a fourteenth embodiment.

A fourteenth embodiment will be described. The embodiment is obtained by modifying the thirteenth embodiment so that a magnetic member 7i is joined to the permanent magnet 4i as shown in FIG. 22. The magnetic member 7i is joined to a pole of the permanent magnet 4i which is on the side of the plate-like member 18, and has two projections which elongate along the side faces of the permanent magnet 4i. The tip end faces of the projections are in the same plane as the other pole of the permanent magnet 4i. The magnetic member 7i is made of a magnetic material which has a high magnetic permeability and a high saturation magnetization. The other components are configured in the same manner as those of the thirteenth embodiment and hence designated by the same reference numerals.

According to the embodiment, a magnetic field can be efficiently applied to a living body by using a single permanent magnet.

Figure 23:
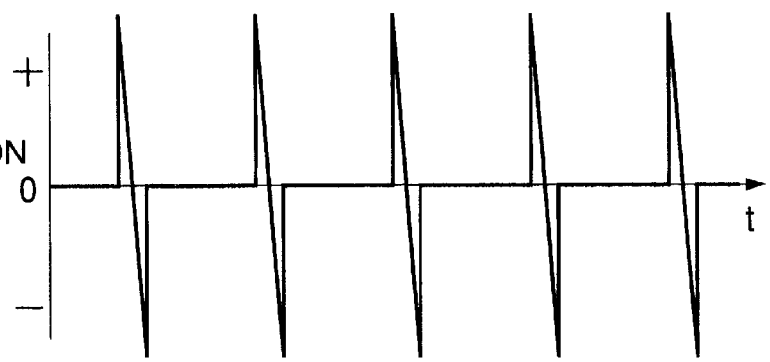
FIG. 23 is a view showing the level of eddy currents generated in the living body according to the fourteenth embodiment.

FIG. 23 shows eddy currents in the living body due to the generation of an induced electromotive force e according to fourteenth embodiment.

Figure 24:
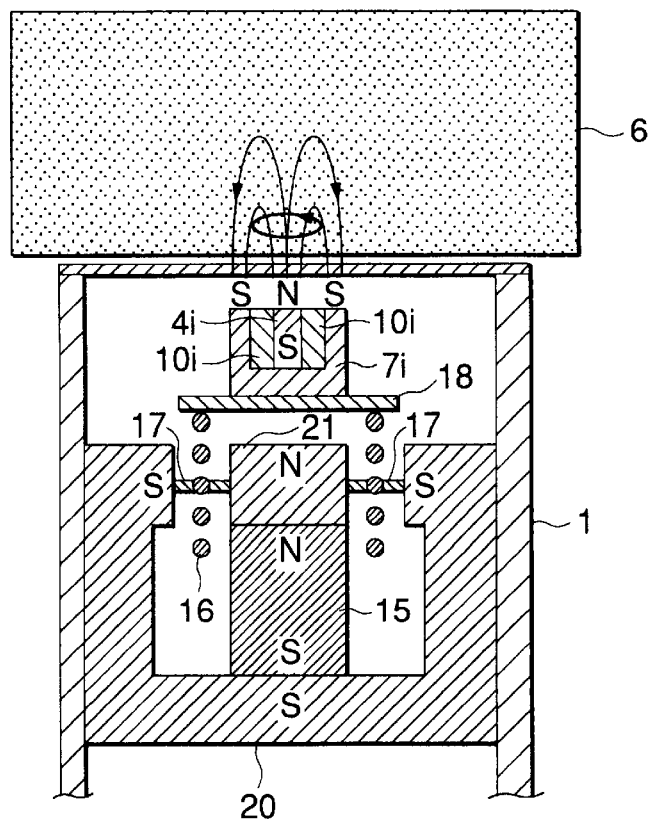
FIG. 24 is a view showing the configuration of a fifteenth embodiment.

A fifteenth embodiment will be described. The embodiment is obtained by modifying the thirteenth embodiment so that a diamagnetic member 10i is disposed between the permanent magnet 4i and the magnetic member 7i as shown in FIG. 24. The other components are configured in the same manner as those of the fourteenth embodiment and hence designated by the same reference numerals.

According to the fifteenth embodiment, since the diamagnetic member 10i is disposed between the permanent magnet 4i and the magnetic member 7i, magnetic fluxes from the N-pole to the S-pole detour, with the result that magnetic fluxes enter not only the surface of the living body 6 but also a deep portion of the living body. Therefore, eddy currents can be generated in a deep portion of the living body 6.

Figure 25:
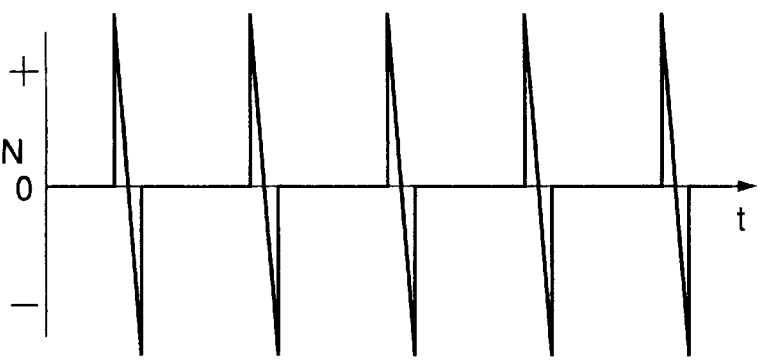
FIG. 25 is a view showing the level of eddy currents generated in the living body according to the fifteenth embodiment.

FIG. 25 shows eddy currents in the living body due to the generation of an induced electromotive force e according to fifteenth embodiment.

Figure 26:
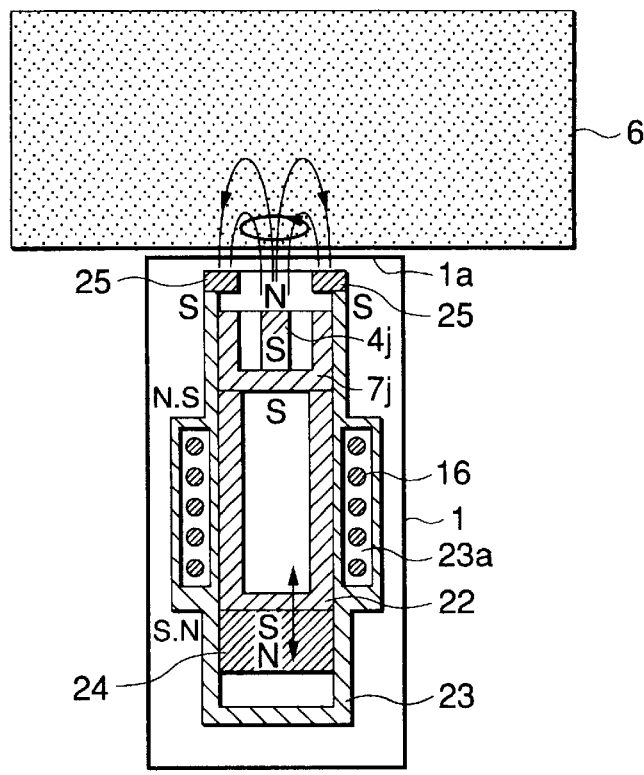
FIG. 26 is a view showing the configuration of a sixteenth embodiment.

A sixteenth embodiment will be described. Also in the embodiment, the same principle as that of a loudspeaker is used. Unlike the above-described embodiments of the loudspeaker type, however, the coil is stationary and the permanent magnet is movable. FIG. 26 shows the configuration of the apparatus. A guide member 23 is fixed to the inside of the case 1. A cylindrical member 22 is disposed so as to be able to reciprocate inside the guide member 23. A coil housing portion 23a is disposed in a middle portion of the guide member 23. The coil 16 is housed in the coil housing portion and fixed thereto. All the case 1, the guide member 23, and the cylindrical member 22 are made of plastic. A permanent magnet 24 is attached to one end portion of the cylindrical member 22, and a magnetic member 7j is attached to the other end portion of the cylindrical member 22. The magnetic member 7j has a U-like section shape. The end portions of the magnetic member are directed toward a wall 1a of the case 1 on the side which is to be made closer to the living body 6. The magnetic member 7j is made of a magnetic material which has a high magnetic permeability and a high saturation magnetization. A permanent magnet 4j upstands from the center of the magnetic member 7j. A stopper 25 which prevents the magnetic member 7j from popping out is disposed inside the end portion of the guide member 23 adjacent to the wall 1a. The opposite end portion of the guide member 23 has a bottom which serves as a stopper for the permanent magnet 24. Also in the embodiment, a control unit and a power source circuit (both are not shown) which are used for supplying a pulse current are connected to the coil 16. The direction of the pulse current may be fixed to one direction, or alternatingly changed to two directions. The control unit controls the period of the pulse current. The period can be set by the operator. The opposing poles of the permanent magnets 4j and 24 have the same polarity. In the embodiment, the case 1 serves as the support unit, the cylindrical member 22 serves as the magnet holding member, and the coil 16, the permanent magnet 24, the control unit, and the power source circuit constitute the reciprocating means.

In the embodiment, the coil 16 is fixed. When a current flows through the coil 16, the coil 16 functions as a magnet in which the N- and S-poles are alternatingly formed with respect to the permanent magnets 4j. This is applicable also to the permanent magnet 24. In the arrangement of the poles of the permanent magnets 4j and 24 shown in FIG. 26, for example, when the portion of the coil 16 on the side of the permanent magnet 4j constitutes the N-pole, the portion of the coil 16 on the side of the permanent magnet 24 constitutes the S-pole. Therefore, the permanent magnets 4j receives an attractive force from the coil 16 and the permanent magnet 24 receives a repulsive force from the coil 16. When the portion of the coil 16 on the side of the permanent magnet 4j constitutes the S-pole, the permanent magnets 4j and 24 receive forces opposite to those mentioned above, respectively. In this way, the permanent magnet 4j repeatedly approaches and separates from the living body 6. As a result, in the living body 6, a varying magnetic field in which the magnetic flux density varies is formed and eddy currents are generated.

In the embodiment, unlike the above-described embodiments of the coil-moving type, the coil 16 is not enclosed by permanent magnets. Consequently, the apparatus can be miniaturized. In the embodiment, the permanent magnet 24 plays an auxiliary role. In the case where the structure is to be simplified or the number of parts is to be reduced, therefore, the permanent magnet may be omitted.

Figure 27:
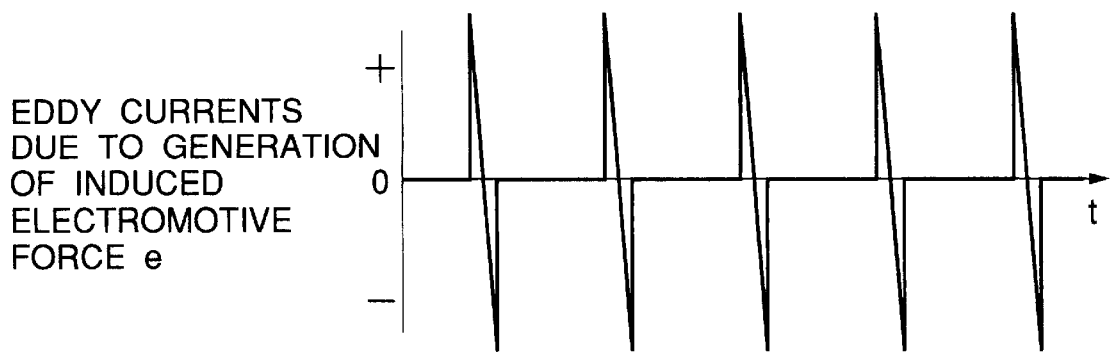
FIG. 27 is a view showing the level of eddy currents generated in the living body according to the sixteenth embodiment.
Figure 28:
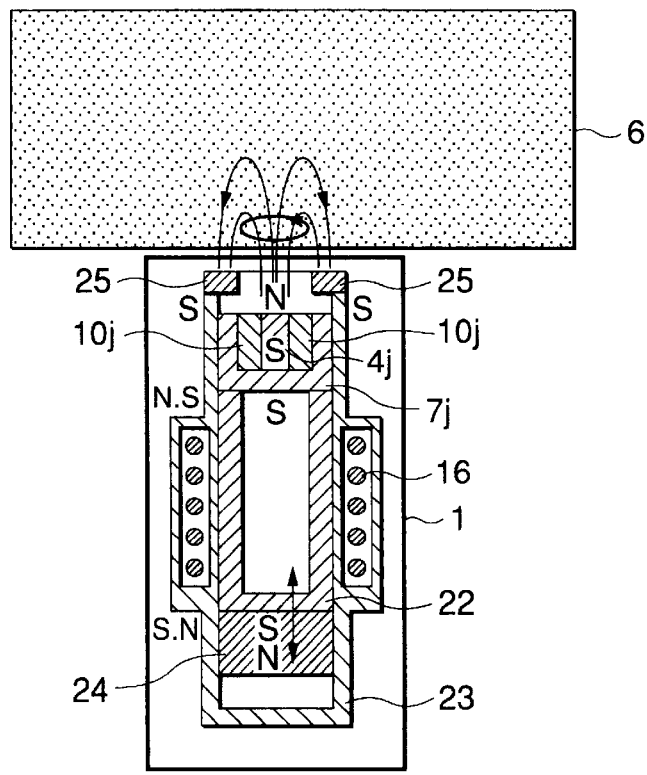
FIG. 28 is a view showing the configuration of a seventeenth embodiment.

FIG. 27 shows eddy currents in the living body due to the generation of an induced electromotive force e according to sixteenth embodiment.

A seventeenth embodiment will be described. The embodiment is different from the sixteenth embodiment in that a diamagnetic member 10j is disposed between the permanent magnet 4j and the magnetic member 7j. The other components are configured in the same manner as those of the sixteenth embodiment.

In the embodiment, the disposition of the diamagnetic member 10j causes magnetic fluxes from the N-pole to the S-pole to detour, with the result that magnetic fluxes enter not only the surface of the living body 6 but also a deep portion of the living body. Therefore, eddy currents can be generated in a deep portion of the living body 6.

Figure 29:
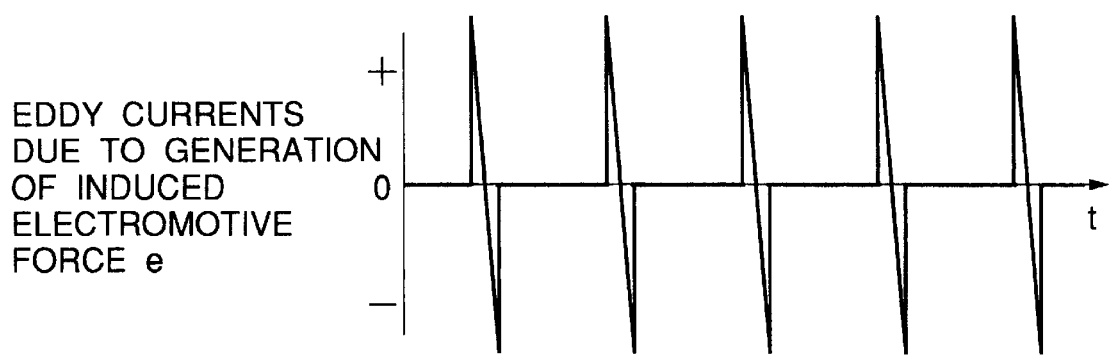
FIG. 29 is a view showing the level of eddy currents generated in the living body according to the seventeenth embodiment.

FIG. 29 shows eddy currents in the living body due to the generation of an induced electromotive force e according to seventeenth embodiment.

Figure 30:
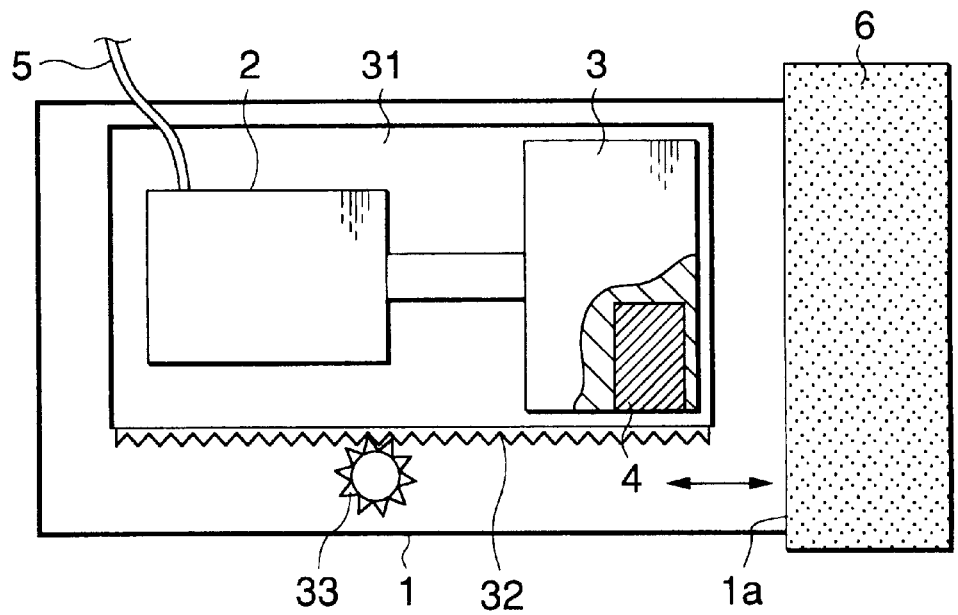
FIG. 30 is a view showing the configuration of an eighteenth embodiment.

An eighteenth embodiment will be described. In the embodiment, as shown in FIG. 30, a base 31 which is slidably held so as to approach and separate from one wall 1a of a plastic case 1 is disposed in the case 1. A rack 32 is attached to the base 31. A pinion 33 which meshes with the rack 32 is attached to the case 1 via a shaft. The shaft of the pinion 33 is projected to the outside of the case 1, and a knob is attached to the tip end of the shaft. When the operator rotates the knob, the base 31 can be moved in the case 1.

A motor 2 is attached to the base 31. A drum-like magnet holding member 3 is attached to the rotation shaft of the motor 2. A permanent magnet 4 is held by the magnet holding member 3. The motor 2 is connected to a control unit and a power source circuit (both are not shown) which are disposed outside the case 1, via a cord 5.

According to this embodiment, the operator rotates the knob to adjust the distance between the permanent magnet 4 and the wall 1a of the case 1. When the apparatus is to be used, the apparatus is caused to abut against the living body 6 as shown in FIG. 30 to attain a stable state. The knob is rotated under this state, whereby the distance between the living body 6 and the permanent magnet 4 can be changed to a desired value. When the distance is increased, for example, the strength of the magnetic field in the living body 6 is reduced and also the level of eddy currents generated in the living body 6 is reduced. By contrast, when the distance is reduced, the strength of the magnetic field in the living body 6 is increased and also the level of eddy currents generated in the living body 6 is increased. The strength of a magnetic field is inversely proportional to the cube of the distance from a magnet. When it is assumed that the strength of the magnetic field due to a permanent magnet is constant, therefore, the simplest way is attained by the present method in which the strength of the magnetic field applied to the living body is changed by adjusting the distance between the living body and the magnet.

Figure 32:
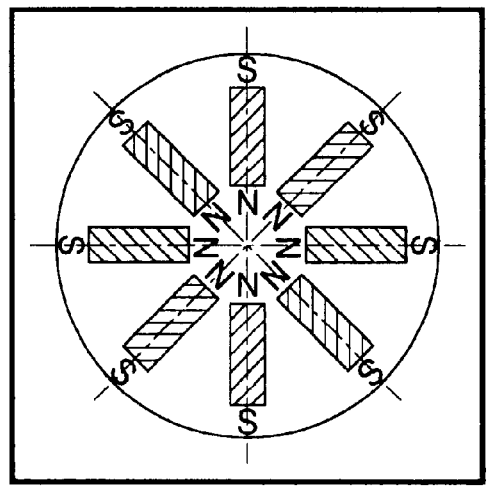
FIGS. 32 and 33 are views showing another embodiment of the arrangement of the permanent magnets or the magnet members.
Figure 33:
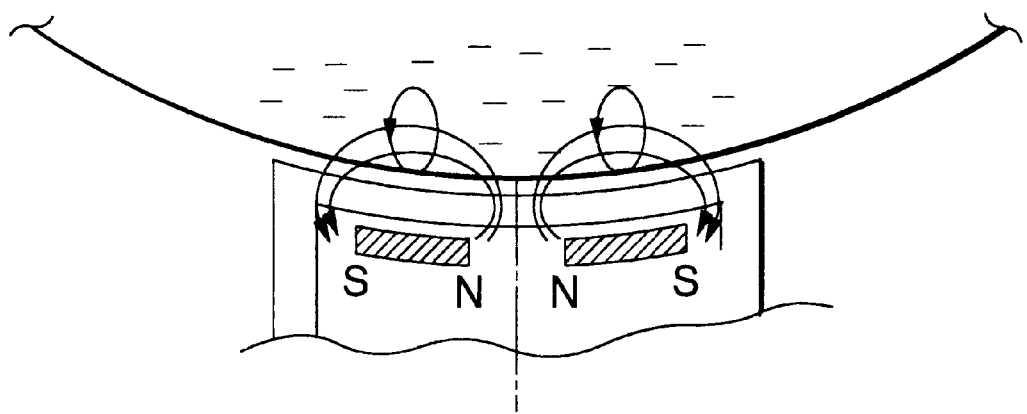

In the eighteenth embodiment described above, the arrangement of the permanent magnet or the magnetic member employs one or two pieces. Of course, it is applicable for employing a plurality of these members and these members could be arranged in a radius as shown in FIG. 32. In this case, it is required that a verification of the magnetic applied to the living body is effectively changed in the preferable field by rotation of the magnet holding member under the condition a preferable gap is defined between the permanent magnets or the magnetic members. According to the radial arrangement, the stimulation frequency could be obtained as several times as the permanent magnet or the magnetic member with respect to the magnet holding member. On the other hand, a surface of the case confronted with the living body is curve shaped along with the living body as shown in FIG. 33.

Figure 31:
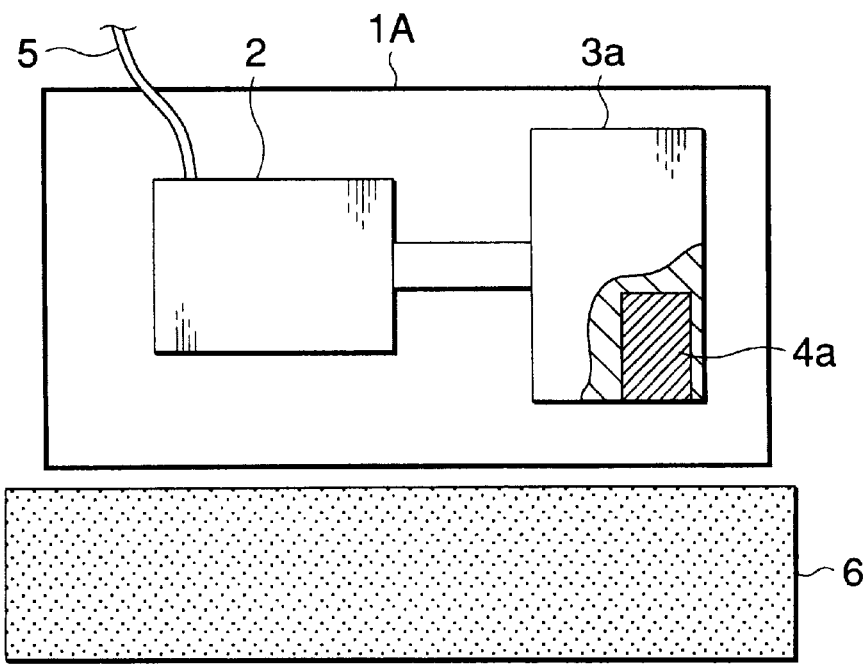
FIG. 31 is a view showing illustrating a state of using a magnetic stimulating apparatus in which a case is cylindrical.

In the embodiments described above, the case 1 has a box-like (rectangular parallelpiped) shape. Alternatively, the case may have a cylindrical shape. In the case of a cylindrical case, when the apparatus is used while setting the center line of the rotation of the magnet holding member 3a to be parallel with the surface of the living body as shown in FIG. 31, the apparatus can be placed so that the surface of the living body having a curvature covers the peripheral face of the apparatus, whereby a magnetic field can be efficiently applied to the living body. In FIG. 31, a case 1A is cylindrical, and the other components are configured in the same manner as those of the apparatus shown in FIG. 1.

In the embodiments described above, the control unit and the power source circuit are disposed outside and separated from the case. Alternatively, they may be disposed inside the case, or a power source circuit having batteries may be disposed in the case so as to constitute a cordless system.

In the embodiments using a motor, the magnet holding member is directly attached to the rotation shaft of the motor. Alternatively, the rotation shaft may be provided with a gear mechanism and the magnet holding member may be attached to the rotation shaft via the gear mechanism. In the alternative, gears are selected by the operation of the operator so that the rotational speed of the magnet holding member is changed.

The apparatus of each of the embodiments is used with being held while a hand. Alternatively, the apparatus may be configured so as to be supported by a support tool.

Figure 34:
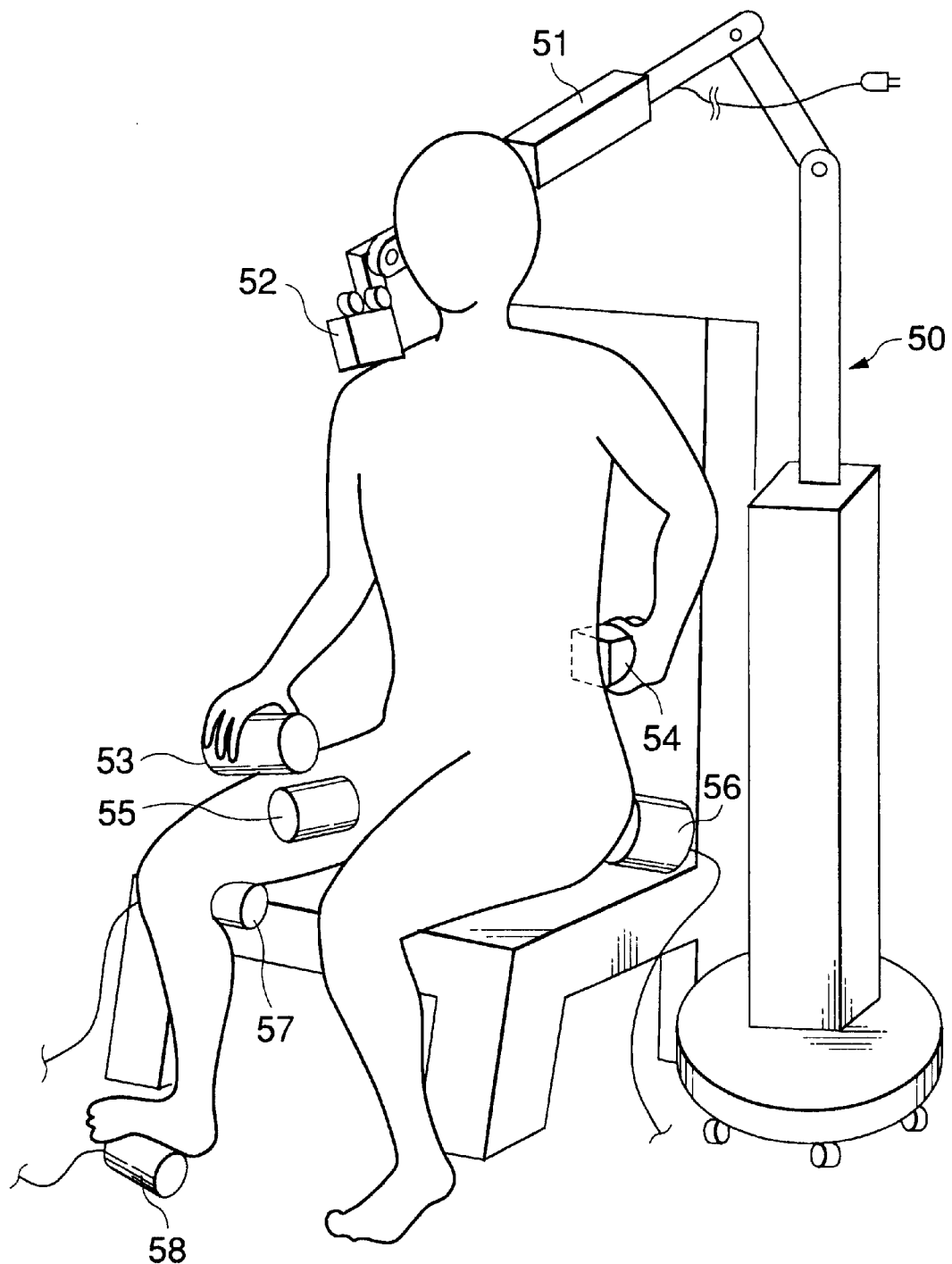
FIG. 34 is a view showing a state of using magnetic stimulating apparatuses.

FIG. 34 shows a state of using the magnetic stimulating apparatuses of the embodiments described above. Magnetic stimulating apparatuses 51 and 52 are of the type in which an apparatus is held by a support tool 50, magnetic stimulating apparatuses 53, 54, and 55 are of the type in which an apparatus incorporates batteries and is held with hand, and magnetic stimulating apparatuses 56, 57, and 58 are of the type in which an apparatus is powered from the outside via a cord and is held with hand.

The invention can attain effects such as: (1) the apparatus does not generate heat and hence a large cooling equipment is not required; (2) the efficiency of the generation of a pulsative magnetic field is improved; (3) the power consumption is reduced; (4) the noise level is lowered; (5) the apparatus can be miniaturized; and (6) the space for treatment is ensured in a treatment room.

The invention can attain further effects such as: (a) the magnetic flux density and the total number of magnetic fluxes can be increased by joining a magnetic member to a permanent magnet; and (b) the magnetic flux density and the total number of magnetic fluxes can be increased by disposing a diamagnetic member in the periphery of a permanent magnet. Moreover, The increased magnetic flux density and total number of magnetic fluxes enable eddy currents to be generated in a deep portion of the living body, and the miniaturization of the apparatus and the reduction of the power consumption to be further enhanced.

Furthermore, since magnetic fluxes generated from a permanent magnet can be easily concentrated by changing the shape of a magnetic member to be joined, magnetic fluxes can be concentrated into a specific region of the living body to stimulate the region in a higher degree than the case of the prior art method using a coil. As a result of the concentration of magnetic fluxes, the magnetic field less affects regions other than the region to be stimulated, such as the brain. Therefore, the safety of the treatment can be enhanced.

What is claimed is:

1. A magnetic stimulating apparatus for a living body comprising:
    a permanent magnet which applies a magnetic field to a living body;
    a magnetic member having projections which extend toward the living body; and
    a magnet moving unit which moves said permanent magnet with respect to said living body.

2. A magnetic stimulating apparatus for a living body according to claim 1, wherein said magnetic member is attached to at least one of poles of said permanent magnet, said magnetic member being high in magnetic permeability and saturation magnetization.

3. A magnetic stimulating apparatus for a living body according to claim 2, wherein a cross section of a portion of said magnetic member is reduced in size as said magnetic member moves towards the living body.

4. The magnetic stimulating apparatus according to claim 2, wherein said projections which extend toward the living body sandwich the permanent magnet therebetween.

5. A magnetic stimulating apparatus for a living body according to claim 1, wherein said permanent magnet includes at least one pair of permanent magnet members, said pair of permanent magnet members are disposed in a state where poles of the same kind are opposed to each other.

6. The magnetic stimulating apparatus according to claim 5, further including a magnetic holding member for holding said permanent magnets, wherein said permanent magnets have a rod-like shape and extend in a radial direction of said magnetic holding member.

7. The magnetic stimulating apparatus according to claim 5, wherein said pair of permanent magnet members are disposed such that poles of the same kind are opposed to each other.

8. The magnetic stimulating apparatus according to claim 7, further comprising a second magnetic member joined to the other pole of said permanent magnet and diamagnetic members disposed between said permanent magnet and said projections of said magnetic member.

9. The magnetic stimulating apparatus according to claim 5, wherein said permanent magnets are formed in the shape of a semicircular arc.

10. The magnetic stimulating apparatus according to claim 9, further including a diamagnetic member disposed between said permanent magnets.

11. A magnetic stimulating apparatus for a living body according to claim 1, further comprising:
    a diamagnetic member which is adjacent to said permanent magnet, disposed between the living body and said permanent magnet and which guides a direction of magnetic fluxes generated from said permanent magnet in a predetermined direction.

12. The magnetic stimulating apparatus according to claim 11, further including a pair of magnetic members disposed adjacent to north and south poles of said permanent magnet and extending toward the living body.

13. A magnetic stimulating apparatus for a living body according to claim 1, wherein said magnet moving unit includes rotating means for rotating said permanent magnet.

14. A magnetic stimulating apparatus for a living body according to claim 13, wherein said rotating means includes a magnet holding member which holds said permanent magnet and a motor which rotates said magnet holding member.

15. A magnetic stimulating apparatus for a living body according to claim 1, wherein said magnet moving unit includes reciprocating member for reciprocating said permanent magnet.

16. A magnetic stimulating apparatus for a living body according to claim 8, wherein said reciprocating member includes:
    a magnet holding member to which said permanent magnet is attached;
    a conductive coil which is attached to said magnet holding member;
    a power source circuit which supplies to said coil a current which periodically changes; and
    a permanent magnet which applies a magnetic field to said coil.

17. The magnetic stimulating apparatus according to claim 16, further comprising a magnetic member disposed between said magnetic holding member and a first pole of said permanent magnet, said magnetic member having two projections which extend along opposite sides of said permanent magnet.

18. The magnetic stimulating apparatus according to claim 17, wherein tip end faces of said projections substantially lie in the same plane as a second pole of said permanent magnet.

19. The magnetic stimulating apparatus according to claim 18, further comprising a diamagnetic member disposed between said permanent magnet and said magnetic member.

20. A magnetic stimulating apparatus for a living body according to claim 15, wherein said reciprocating member includes:

a magnet holding member to which said permanent magnet is attached;

a guide unit which guides said magnet holding member so as to reciprocate in predetermined directions;

a conductive coil for reciprocating said magnet holding member; and a power source circuit which supplies to said coil a current which periodically changes.

21. A magnetic stimulating apparatus for a living body according to claim 1, further comprising:

a moving mechanism unit which moves said magnet moving unit in a predetermined direction.

22. A magnetic stimulating apparatus for a living body comprising:

a variable magnetic field generating unit including:

a permanent magnet which applies a magnetic field to a living body;

a magnet moving unit which moves said permanent magnet; and a magnetic field transmitting unit which is separated from said variable magnetic field generating unit and disposed between said variable magnetic field generating unit and the living body, wherein said magnetic field transmitting unit is adapted to be disposed on or in a living body and comprises a magnetic member which transmits a magnetic field to the living body.

23. A magnetic stimulating apparatus for a living body comprising:

a rotating member; and plural magnetic force generating members which respectively hold along a peripheral face different numbers of permanent magnets for applying a magnetic field to the living body, said plural magnetic force generating members are separately detachable and attachable with respect to a rotation shaft of said rotating means thereby to change the frequency of the magnetic field applied to the living body.

24. A magnetic stimulating apparatus for a living body comprising:

plural permanent magnets which apply a magnetic field to a living body;

a magnet holding member for holding a different number of said permanent magnets along a peripheral face thereby to change the frequency of the magnetic field applied to the living body; and rotating mechanism to which said magnet holding member is attached via a rotation shaft, wherein at least one of said permanent magnets is detachable with respect to said magnet holding member.

25. A magnetic stimulating apparatus for a living body comprising:

a rotating member; and plural magnetic force generating members which respectively hold along a peripheral face permanent magnets for applying a magnetic field to a living body, and which are detachable with respect to a rotation shaft of said rotating member, said permanent magnets held by each of said magnetic force generating members being different in size from said permanent magnets held by the other magnetic force generating members so that the pulse width of the magnetic field produced by each of said permanent magnets is different.

26. A magnetic stimulating apparatus for a living body comprising:

plural permanent magnets which apply a magnetic field to a living body and which are different from each other in size so that the pulse width of the magnetic field produced by each of said permanent magnets is different;

a magnet holding member which detachably holds at least one of said permanent magnets along a peripheral face; and a rotating member to which said magnet holding member is attached via a rotation shaft.

27. A magnetic stimulating apparatus for a living body comprising:

a case for holding said magnetic stimulating apparatus;

a guide member fixed to said case, said guide member having a coil disposed therein;

a cylindrical member which is reciprocatable in said guide member, said cylindrical member having two end portions;

a first permanent magnet disposed on an end portion of said cylindrical member which faces the living body;

a second permanent magnet disposed on the other end portion of said cylindrical member; and a coil disposed in said guide member for conducting a current therethrough thereby to cause said first permanent magnet to reciprocate relative to the living body.

28. A magnetic stimulating apparatus for a living body comprising:

at least one magnetic member having a projection which extends toward the living body;

a diamagnetic member which is adjacent to said magnetic member for allowing lines of magnetic force reach a deep position in the living body.

29. The magnetic stimulating apparatus according to claim 28, wherein a cross section of a portion of said magnetic member is reduced in size as said magnetic member extends towards the living body.

30. The magnetic stimulating apparatus according to claim 29, wherein, said magnetic member includes a plurality of projections, said diamagnetic member is disposed adjacent to said projections for preventing lines of magnetic force from being generated along a short path between said projections and allowing lines of magnetic force to reach a deep position in the living body.

31. The magnetic stimulating apparatus according to claim 30, wherein said diamagnetic member is disposed between said projections.

32. A method for treating incontinence comprising steps of:

applying at least one magnetic member having a projection which extends toward a living body to the living body;

generating a varying magnetic filed to said living body such that eddy currents are generated in said living body.

33. The method for treating incontinence according to claim 32, wherein a cross section of a portion of said magnetic member is reduced in size as said magnetic member extends towards the living body.

34. The method for treating incontinence according to claim 32, wherein a diamagnetic member is disposed adjacent to said magnetic member for allowing lines of magnetic force to reach a deep position in said living body.

35. The method for treating incontinence according to claim 32, wherein
    said magnetic member includes a plurality of projections, further including the step of
    dispensing a diamagnetic member adjacent to said projections for preventing lines of magnetic force from being generated along a short path between said projections and allowing lines of magnetic force reach a deep position in the living body.

36. The method for treating incontinence according to claim 32, wherein said diamagnetic member is disposed between said projections.

* * * * *